(12) United States Patent
Chen et al.

(10) Patent No.: US 11,946,041 B2
(45) Date of Patent: Apr. 2, 2024

(54) MODIFICATION OF POLYPEPTIDES

(71) Applicant: BicycleRD Limited, Cambridge (GB)

(72) Inventors: Liuhong Chen, Cambridge (GB); Michael Skynner, Cambridge (GB); Amy Brown, Cambridge (GB); James Cooke, Cambridge (GB); Rachid Lani, Cambridge (GB)

(73) Assignee: BicycleRD Limited, Cambridge (GB)

( * ) Notice: Subject to any disclaimer, the term of this patent is extended or adjusted under 35 U.S.C. 154(b) by 2 days.

(21) Appl. No.: 16/607,378

(22) PCT Filed: Apr. 24, 2018

(86) PCT No.: PCT/EP2018/060498
§ 371 (c)(1),
(2) Date: Oct. 23, 2019

(87) PCT Pub. No.: WO2018/197509
PCT Pub. Date: Nov. 1, 2018

(65) Prior Publication Data
US 2020/0407709 A1    Dec. 31, 2020

(30) Foreign Application Priority Data

Apr. 24, 2017  (GB) ..................................... 1706477

(51) Int. Cl.
*C12N 15/10*    (2006.01)
(52) U.S. Cl.
CPC ................................ *C12N 15/1037* (2013.01)
(58) Field of Classification Search
None
See application file for complete search history.

(56) References Cited

U.S. PATENT DOCUMENTS 2,642,514 A    6/1953    Herkenhoff

FOREIGN PATENT DOCUMENTS

| EP | 2393520 B1 | 7/2015 |
| EP | 2970954 B1 | 10/2018 |
| GB | 1239978 A | 7/1971 |
| WO | 1997008320 A1 | 3/1997 |
| WO | 2004077062 A2 | 9/2004 |
| WO | 2006078161 A1 | 7/2006 |
| WO | 2009098450 A2 | 8/2009 |
| WO | 2010089115 A1 | 8/2010 |
| WO | WO 2016/067035 | * 10/2016 |

OTHER PUBLICATIONS

Hart et al (JBC 269:12468-74) (Year: 1994).*
Barbas et al., "Semisynthetic combinatorial antibody libraries: a chemical solution to the diversity problem," Proceedings of the National Academy of Sciences of the United States of America, vol. 89, No. 10, May 1992 (pp. 4457-4461).
Biron et al., "Improving oral bioavailability of peptides by multiple N-methylation: somatostatin analogues," Angew. Chem. Int. Ed., vol. 47, No. 14, Mar. 2008 (pp. 2595-2599).
Chen and Harrison, "Cell-penetrating peptides in drug development: enabling intracellular targets," Biochemical Society Transactions, vol. 35, No. 4, Jul. 2007 (pp. 821-825).
Cherney et al., "Macrocyclic Amino Carboxylates as Selective MMP-8 Inhibitors," Journal of Medicinal Chemistry, vol. 41, No. 11, May 1998 (pp. 1749-1751).
Crameri et al., "Construction and evolution of antibody-phage libraries by DNA shuffling," Nature Medicine, vol. 2, No. 1, Jan. 1996 (pp. 100-102).
Davies and Riechmann, "Antibody VH Domains as Small Recognition Units," Nature Biotechnology, vol. 13, No. 5, May 1995 (pp. 475-479).
De Kruif et al., "Selection and Application of Human Single Chain Fv Antibody Fragments from a Semi-synthetic Phage Antibody Display Library with Designed CDR3 Regions," Journal of Molecular Biology, vol. 248, No. 1, Apr. 1995 (pp. 97-105).
Derossi et al., "The third helix of the Antennapedia homeodomain translocates through biological membranes," Journal of Biological Chemistry, vol. 269, No. 14, Apr. 1994 (pp. 10444-10450).
Driggers et al., "The exploration of macrocycles for drug discovery—an underexploited structural class," Nature Reviews Drug Discovery, vol. 7, No. 7, Jul. 2008 (pp. 608-624).
Elson-Schwab et al., "Guanidinylated Neomycin Delivers Large, Bioactive Cargo into Cells through a Heparan Sulfate-dependent Pathway," Journal of Biological Chemistry, vol. 282, No. 18, May 2007 (pp. 13585-13591).
Fiacco and Roberts, "N-Methyl Scanning Mutagenesis Generates Protease-Resistant G Protein Ligands with Improved Affinity and Selectivity," ChemBioChem, vol. 9, No. 14, Sep. 2008 (pp. 2200-2203).
Gentilucci et al., "Chemical modifications designed to improve peptide stability: incorporation of non-natural amino acids, pseudo-peptide bonds, and cyclization," Current Pharmaceutical Design, vol. 16, No. 28, No Month Listed 2010 (pp. 3185-3203).
Griffiths et al., "Isolation of high affinity human antibodies directly from large synthetic repertoires," EMBO Journal, vol. 13, No. 14, Jul. 1994 (pp. 3245-3260).

(Continued)

*Primary Examiner* — Christopher M Gross
(74) *Attorney, Agent, or Firm* — Dechert LLP; Andrea L. C. Reid; Gang Wang

(57) ABSTRACT

The invention relates to a method for screening a library of peptide ligands, said library comprising a plurality of polypeptides covalently linked to a molecular scaffold at two or more amino acid residues, comprising the steps of displaying said library of peptide ligands in a genetic display system, wherein the polypeptide comprises two or more reactive groups which form a covalent linkage to the molecular scaffold, and at least one loop which comprises a sequence of amino acids subtended between two of said reactive groups; exposing the peptide ligands to one or more cells which display one or more target molecules on the cell surface; and screening the peptide ligands for binding against the target, and selecting the ligands which bind to the target.

17 Claims, 12 Drawing Sheets

Specification includes a Sequence Listing.

(56) References Cited

OTHER PUBLICATIONS

Gupta et al., "Intracellular delivery of large molecules and small particles by cell-penetrating proteins and peptides," Advanced Drug Delivery Reviews, vol. 57, No. 4, Feb. 2005 (pp. 637-651).
Heinis et al., "Phage-encoded combinatorial chemical libraries based on bicyclic peptides," Nature Chemical Biology, vol. 5, No. 7, Jul. 2009 (pp. 502-507).
Hess et al., "Backbone Cyclic Peptidomimetic Melanocortin-4 Receptor Agonist as a Novel Orally Administrated Drug Lead for Treating Obesity," Journal of Medicinal Chemistry, vol. 51, No. 4, Jan. 2008 (pp. 1026-1034).
Hoogenboom and Winter, "By-passing immunisation. Human antibodies from synthetic repertoires of germline VH gene segments rearranged in vitro," Journal of Molecular Biology, vol. 227, No. 2, Sep. 1992 (pp. 381-388).
Ide and Ichikawa, "A novel method for artificial lipid-bilayer formation," Biosensors and Bioelectronics, vol. 21, No. 4, Jan. 2005 (pp. 672-677).
International Search Report and Written Opinion issued by the European Patent Office as International Searching Authority for International Application No. PCT/EP2018/060498, dated Jul. 5, 2018 (13 pages).
Jespers et al., "Selection of optical biosensors from chemisynthetic antibody libraries," Protein Engineering Design and Selection, vol. 17, No. 10, Oct. 2004 (pp. 709-713).
Jones et al., "Targeting membrane proteins for antibody discovery using phage display," Scientific Reports, vol. 6, No. 1, May 2016 (pp. 1-11).
Kanazawa et al., "Non-obese-diabetic mice: immune mechanisms of pancreatic β-cell destruction," Diabetologia, vol. 27, Jul. 1984 (pp. 113-115).
Kemp and McNamara, "Conformationally restricted cyclic nonapeptides derived from L-cysteine and LL-3-amino-2-piperidone-6-carboxylic acid (LL-Acp), a potent .beta.-turn-inducing dipeptide analog," Journal of Organic Chemistry, vol. 50, No. 26, Dec. 1985 (pp. 5834-5838).
Khan et al., "Engineering Lipid Bilayer Membranes for Protein Studies," International Journal of Molecular Sciences, vol. 14, No. 11, Nov. 2013 (pp. 21561-21597).
Knight and Adams, "Three genes for lupus nephritis in NZB x NZW mice," Journal of Experimental Medicine, vol. 147, No. 6, Jun. 1978 (pp. 1653-1660).
Lani et al., "Identification of high affinity, highly selective bicyclic peptides (Bicycles®) to transmembrane proteins using phage display screening on whole cells," Abstract, PEGS Summit, Boston, Massachusetts, May 2017 (1 page).
Linde et al., "Structure-Activity Relationship and Metabolic Stability Studies of Backbone Cyclization and N-Methylation of Melanocortin Peptides," Biopolymers, vol. 90, No. 5, No. Month Listed 2008 (pp. 671-682).
Lindstrom et al., "Myasthenia gravis," Advances in Immunology, vol. 42, Dec. 1988 (pp. 233-284).
Marks et al., "By-passing immunization. Human antibodies from V-gene libraries displayed on phage," Journal of Molecular Biology, vol. 222, No. 3, Dec. 1991 (pp. 581-597).
Maron and Cohen, "H-2K mutation controls immune response phenotype of autoimmune thyroiditis. Critical expression of mutant gene product in both thymus and thyroid glands," Journal of Experimental Medicine, vol. 152, No. 4, Oct. 1980 (pp. 1115-1120).
McFarlin et al., "Experimental Allergic Encephalomyelitis in the Rat: Response to Encephalitogenic Proteins and Peptides," Science, vol. 179, No. 4072, Feb. 1973 (pp. 478-480).

Mullis and Faloona, "Specific synthesis of DNA in vitro via a polymerase-catalyzed chain reaction," Methods in Enzymology, vol. 155, Jan. 1987 (pp. 335-350).
Nestor, "The medicinal chemistry of peptides," Current Medicinal Chemistry, vol. 16, No. 33, Oct. 2009 (pp. 4399-4418).
Nissim et al., "Antibody fragments from a 'single pot' phage display library as immunochemical reagents," EMBO Journal, vol. 13, No. 3, Feb. 1994 (pp. 692-698).
Oehlke et al., "Cellular uptake of an alpha-helical amphipathic model peptide with the potential to deliver polar compounds into the cell interior non-endocytically," Biochimica et Biophysica Acta, vol. 1414, No. 1-2, Nov. 1998 (pp. 127-139).
Okuyama, "Small-molecule mimics of an a-helix for efficient transport of proteins into cells," Nature Methods, vol. 4, No. 2, Feb. 2007 (pp. 153-159).
Pavlidou et al., "Nanodiscs Allow Phage Display Selection for Ligands to Non-Linear Epitopes on Membrane Proteins," PLoS One, vol. 8, No. 9, Sep. 2013 (8 pages).
Reinertsen et al., "B-Lymphocyte Alloantigens Associated with Systemic Lupus Erythematosus," New England Journal of Medicine, vol. 299, No. 10, Sep. 1978 (pp. 515-518).
Satoh et al., "Experimental allergic encephalomyelitis mediated by murine encephalitogenic T cell lines specific for myelin proteolipid apoprotein," Journal of Immunology, vol. 138, No. 1, Jan. 1987 (pp. 179-184).
Steck et al., "Inside-out red cell membrane vesicles: preparation and purification," Science, vol. 168, No. 3928, Apr. 1970 (pp. 255-257).
Stuart et al., "Collagen Autoimmune Arthritis," Annual Review of Immunology, vol. 2, No. Month Listed 1984 (pp. 199-218).
Timmerman et al., "Rapid and quantitative cyclization of multiple peptide loops onto synthetic scaffolds for structural mimicry of protein surfaces," Chembiochem, vol. 6, No. 5, May 2005 (pp. 821-824).
Tugyi et al., "Partial D-amino acid substitution: Improved enzymatic stability and preserved Ab recognition of a MUC2 epitope peptide," Proceedings of the National Academy of Sciences of the United States of America, vol. 102, No. 2, Jan. 2005 (pp. 413-418).
Van Eden et al., "Cloning of the mycobacterial epitope recognized by T lymphocytes in adjuvant arthritis," Nature, vol. 331, No. 6152, Jan. 1988 (pp. 171-173).
Winter et al., "Making antibodies by phage display technology," Annual Review of Immunology, vol. 12, No Month Listed 1994 (pp. 433-455).
Wu et al., "Structures of the CXCR4 chemokine GPCR with small-molecule and cyclic peptide antagonists," Science, vol. 330, No. 6007, Nov. 2010 (pp. 1066-1071).
Xiong et al., "Crystal structure of the extracellular segment of integrin aVβ3 in complex with an Arg-Gly-Asp ligand," Science, vol. 296, No. 5565, Apr. 2002 (pp. 151-155).
Yoon et al., "An efficient strategy for cell-based antibody library selection using an integrated vector system," BMC Biotechnology, vol. 12, No. 62, Sep. 2012 (10 pages).
Zhao et al., "Structural basis of specificity of a peptidyl urokinase inhibitor, upain-1," Journal of Structural Biology, vol. 160, No. 1, Oct. 2007 (pp. 1-10).
Figure 3.8 of "Immunobiology: The Immune System in Health and Disease," Garland Science, 2001.
Kell, "The Transporter-Mediated Cellular Uptake and Efflux of Pharmaceutical Drugs and Biotechnology Projects: How and Why Phospholipid Bilayer Transport is Negligible in Real Biomembranes," Molecules 2021;26, 5629.

* cited by examiner

17-SC-AS 24 Sept 2014
MMP-14 FP direct & competition

MODIFICATION OF POLYPEPTIDES

REFERENCE TO SEQUENCE LISTING

A Sequence Listing is being submitted electronically via EFS in the form of a text file created Jun. 6, 2018 and named "P5816PC00_SL.txt" (7,763 bytes), the contents of which are incorporated herein by reference in their entirety.

CROSS-REFERENCE TO RELATED APPLICATIONS

This application is a U.S. national stage application under 35 U.S.C. § 371 of International Application No. PCT/EP2018/060498, filed Apr. 24, 2018, which claims priority under 35 U.S.C. § 119 to United Kingdom Application No. GB1706477.5, filed Apr. 24, 2017, each of which is incorporated herein by reference in its entirety.

FIELD OF THE INVENTION

The present invention concerns methods for production of polypeptide ligands having a desired binding activity. In particular, the invention concerns the production of polypeptides which are covalently bound to molecular scaffolds such that two or more peptide loops are subtended between attachment points to the scaffold. Screening of such polypeptides is carried out using a membrane-based screen, which allows screening against antigens in their natural form.

BACKGROUND

Cyclic peptides are able to bind with high affinity and target specificity to protein targets and hence are an attractive molecule class for the development of therapeutics. In fact, several cyclic peptides are successfully used in the clinic, as for example the antibacterial peptide vancomycin, the immunosuppressant drug cyclosporine or the anti-cancer drug ocreotide (Driggers, et al., *Nat Rev Drug Discov* 2008, 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 Å$^2$; Wu, B., et al., *Science* 330 (6007), 1066-71), a cyclic peptide with the Arg-Gly-Asp motif binding to integrin αVb3 (355 Å$^2$) (Xiong, J. P., et al., *Science* 2002, 296 (5565), 151-5) or the cyclic peptide inhibitor upain-1 binding to urokinase-type plasminogen activator (603 Å$^2$; Zhao, G., et al., *J Struct Biol* 2007, 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8, MMP-8) which lost its selectivity over other MMPs when its ring was opened (Cherney, R. J., et al., *J Med Chem* 1998, 41 (11), 1749-51). The favorable binding properties achieved through macrocyclization are even more pronounced in multicyclic peptides having more than one peptide ring as for example in vancomycin, nisin or actinomycin.

Different research teams have previously tethered polypeptides with cysteine residues to a synthetic molecular structure (Kemp, D. S. and McNamara, P. E., J. Org. Chem, 1985; Timmerman, P. et al., ChemBioChem, 2005). Meloen and co-workers had used tris(bromomethyl)benzene and related molecules for rapid and quantitative cyclisation of multiple peptide loops onto synthetic scaffolds for structural mimicry of protein surfaces (Timmerman, P. et al., ChemBioChem, 2005). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

WO2004/077062 discloses a method of selecting a candidate drug compound. In particular, this document discloses various scaffold molecules comprising first and second reactive groups, and contacting said scaffold with a further molecule to form at least two linkages between the scaffold and the further molecule in a coupling reaction.

WO2006/078161 discloses binding compounds, immunogenic compounds and peptidomimetics. This document discloses the artificial synthesis of various collections of peptides taken from existing proteins. These peptides are then combined with a constant synthetic peptide having some amino acid changes introduced in order to produce combinatorial libraries. By introducing this diversity via the chemical linkage to separate peptides featuring various amino acid changes, an increased opportunity to find the desired binding activity is provided. FIG. 1 of this document shows a schematic representation of the synthesis of various loop peptide constructs. The constructs disclosed in this document rely on —SH functionalised peptides, typically comprising cysteine residues, and heteroaromatic groups on the scaffold, typically comprising benzylic halogen substituents such as bis- or tris-bromophenylbenzene. Such groups react to form a thioether linkage between the peptide and the scaffold.

Heinis et al. recently developed a phage display-based combinatorial approach to generate and screen large libraries of bicyclic peptides to targets of interest (Heinis, et al., *Nat Chem Biol* 2009, 5 (7), 502-7; see also international patent application WO2009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule (tris-(bromomethyl)benzene). Bicyclic peptides isolated in selections for affinity to the human proteases cathepsin G and plasma Kallikrein (PK) had nanomolar inhibitory constants. The best inhibitor, PK15, inhibits human PK (hPK) with a K$_i$ of 3 nM. Similarities in the amino acid sequences of several isolated bicyclic peptides suggested that both peptide loops contribute to the binding. PK15 did not inhibit rat PK (81% sequence identity) nor the homologous human serine proteases factor XIa (hfXIa; 69% sequence identity) or thrombin (36% sequence identity) at the highest concentration tested (10 μM) (Heinis, et al., *Nat Chem Biol* 2009, 5 (7), 502-7). This finding suggested that the bicyclic inhibitor possesses high affinity for its target, and is highly specific.

In our copending European patent application EP2970954 we describe an alternative system for assembling libraries of polypeptides, in which the phage-bound polypeptides are attached to a solid phase for modification with the scaffold. In both this system and the system developed by Heinis, however, the phage-bound polypeptides are screened against antigen in solution; this does not represent the native conformation for all potential antigens. Therefore, certain targets may not be tractable to screening using the methods of the prior art.

Membrane-bound proteins and transmembrane proteins are present in their natural conformation in cell membranes and membrane preparations. There is a need, therefore, to screen polypeptides against membrane proteins in situ in a lipid bilayer membrane.

SUMMARY OF THE INVENTION

In a first aspect, the present invention provides a method for screening a library of peptide ligands, said library comprising a plurality of polypeptides covalently linked to a molecular scaffold at two or more amino acid residues, comprising the steps of:
- (a) displaying said library of peptide ligands in a genetic display system, wherein the polypeptide comprises two or more reactive groups which form a covalent linkage to the molecular scaffold, and at least one loop which comprises a sequence of amino acids subtended between two of said reactive groups;
- (b) exposing the peptide ligands to one or more target antigens which are present in a lipid bilayer membrane system; and
- (c) screening the peptide ligands for binding against the target, and selecting the ligands which bind to the target.

In embodiments, the genetic display system is selected from phage display, ribosome display, mRNA display, yeast display and bacterial display. In one embodiment, the genetic display system is phage display.

Preferably, the polypeptide is displayed by fusion to the pIII protein of fd phage, such as fd-tet phage.

The library of peptide ligands has a complexity of at least $10^4$, $10^5$, $10^6$, $10^7$, $10^8$, $10^9$, $10^{11}$ or more peptide ligands. The library size can be at least 10 times the complexity, for example $10^{11}$, $10^{12}$, $10^{13}$ or more peptide ligands.

Libraries of peptide ligands can be prepared according to methods known in the art. For example, methods are described in WO (Winter Heinis) and WO (P4195PC00). The original method by Heinis et al. performed the conjugation of peptide and molecular scaffold (TBMB) in free solution. Phage, bearing peptides which were (or were not) conjugated to the TBMB scaffold were then isolated by centrifugation. Improved results have obtained by conjugating the phage to a solid phase purification resin, which can then be used to isolate the phage. See EP2970954. For example, the resin can be isolated by centrifugation or retained in columns; in a preferred embodiment, the resin is magnetic and can be isolated by the application of a magnetic field. Either conjugation approach can be used with the present invention.

In embodiments, the lipid bilayer system displaying the target molecule, as used herein, refers to cells, cellular membrane fractions or lipid bilayers engineered by treatment with a virus, cellular fragmentation or otherwise synthetically produced where the membrane localisation of the target provide stabilisation of a more representative "native" conformation which is available for screening. Lipid bilayer systems may be provided in the form of whole cells, or cell membrane fractions. The isolation of cell membranes and the preparation of artificial membrane fractions is well known in the art; see, for instance, Khan et al., Int. J. Mol. Sci. 2013, 14, 21561-21597; Ide & Ichikawa, *Biosensors and Bioelectronics* 21 (2005) 672-677. "Inside out" membrane vesicles prepared from erythrocytes are also appropriate for use in the present invention—see Steck, et al., Science (1970) 168(928):255-7. Virus-like particles may be used, such as those available commercially from Integral molecular or the like. Membranes may be derived from eukaryotic cells, such as mammalian cells or yeast cells, and also insect cells and prokaryotic cells.

Cells can be selected from HEK 293F cells, HeLa cells, U2OS cells, A549 cells, HT1080 cells, CAD cells, P19 cells, NIH 3T3 cells, L929 cells, N2a cells, CHO cells, MCF-7 cells, Y79 cells, SO—Rb50 cells, Hep G2 cells, DUKX-X11 cells, J558L cells and BHK cells. Prokaryotic, such as bacterial, cells may also be used, as may yeast and insect cells as well as membrane preparations from any such cells. Any suitable cell or lipid bilayer membrane can be used, as long as it displays the target molecule in a desired configuration; preferably, this is a natural configuration.

In certain embodiments, the cell is a cell which naturally expresses the target molecule and presents it at its surface.

Screening the libraries of the invention against the target molecule arranged on a cell surface may result in the isolation of non-specific binding members of the library as well as specific binding members. Non-specific binding members can be eliminated by "deselecting" the library. The library is deselected by screening against cells not displaying the target molecule.

Multiple rounds of selection against the target molecule and deselection against cells lacking the target molecule can be used to identify improved binding members of the library of peptide ligands. As required, variation at specific and/or random residues may be introduced, to provide selective further variation which can be sued to improve binding specificity and affinity.

The polypeptides can be amplified between rounds of selection. In one embodiment, the polypeptides are amplified by phage infection of bacteria; phage display facilitates amplification and repeated selection by cycles of phage display and infection.

The target molecule may be any desired molecule, but in preferred embodiments is a cell surface molecule or a molecule which is present close to a cell surface. Selection against cells requires the target molecule to be present at the cell surface; accordingly, if the molecule is not naturally arranged at the cell surface, it is preferably modified by attachment to a cell surface protein or cellular component, such that it is present at the cell surface. In embodiments, the target is a binding molecule such as a receptor or ligand; an entity (such as an endogenous ligand or a drug) is directed to and/or binds to the target and may result in a change in behaviour or function. Examples of common classes of targets include receptors, ion channels, solute transporters, enzymes, tumour associated antigens, cell junction proteins, structural proteins, pathological proteins associated and adhesion molecules.

For example, receptors include G protein coupled receptors, T-cell Co-stimulatory receptors, Immune checkpoint inhibitory receptors and receptor tyrosine kinases; ion channels include, ligand gated ion channels and voltage gated ion channels; solute transporters include neutral amino acid transporters, organic anion transporters and urea; adhesion molecules include integrins; Enzymes include matrix metalloproteases, oxido reductases and anhydrases;

G protein coupled receptors include the β1 adrenergic receptor; ligand gated ion channels include the 5HT3 receptor; voltage gated ion channels include the voltage gated calcium channel family which includes the Cav1.2 channel; neutral amino acid transporters include the glutamate transporter; organic anion transporters include OAT1

(SLC22A6); urea transporters include UT-A1; matrix metalloproteases include MMP14; oxido reductases include Cyclooxygenase 2; anhydrases include carbonic anhydrase IX; integrins include avb3; tumour associated antigens include EGFRviii, cell junction proteins include Claudin; structural proteins include tubulin, pathological proteins associated Include tau.

In embodiments, the target molecule is selected from EphA3, β1 Adrenergic receptor, CCR4, CD38, Claudin 18.2 and MT1-MMP.

The invention is particularly useful for selecting peptide ligands cannot be selected against the target molecule in solution. Some molecules do not adopt a native conformation outside of a cellular environment, and for this reason can be difficult to identify peptide ligands which bind to the in a biologically relevant manner. The invention overcomes this difficulty by selecting ligands against molecules which are present in a biological environment. Therefore, the molecules selected according to the invention are more suitable for use in vivo and in medical applications.

Moreover, the invention can be used to identify polypeptide ligands which bind at different sites on a given target molecule, to those sites which may be targeted by selection in solution. Therefore, the diversity of targeting may be increased, providing a greater range of biologically-relevant binding sites on a desired target.

In certain embodiments, the library of peptide ligands is further screened for resistance to protease activity. Proteases are present in in vivo environments and, in certain cases, require the use of protease resistant peptide ligands. Protease resistance can be selected for by exposing the peptide ligands to proteases, as described for example in EP2393520.

In one embodiment, each peptide ligand in the library of peptide ligands comprises three or more reactive groups covalently linked to a molecular scaffold. Three is the preferred number of reactive groups; four of five groups can also be contemplated. In general, peptide ligands with greater number of reactive groups are complex and less amenable to consistent assembly without the formation of isomeric forms.

The peptide ligands may be monospecific, binding to a single target molecule, or multispecific. Multispecific peptide ligands are described in WO2010/089115.

In embodiments, the polypeptide ligands are multispecific. In a first configuration, for example, the polypeptide loops formed by the interaction of the polypeptide with the molecular scaffold are capable of binding to more than one target. Within this configuration, in one embodiment loops may be selected individually for binding to the desired targets, and then combined. In another embodiment, the loops are selected together, as part of a single structure, for binding to different desired targets.

In a second configuration, a functional group may be attached to the N or C terminus, or both, of the polypeptide. The functional group may take the form of a binding group, such as a polypeptide, including an antibody domain, an Fc domain or a further structured peptide as described above, capable of binding to a target. It may moreover take the form of a reactive group, capable of chemical bonding with a target. Moreover, it can be an effector group, including large plasma proteins, such as serum albumin, and a cell penetrating peptide.

In a third configuration, a functional group may be attached to the molecular scaffold itself. Examples of functional groups are as for the preceding configuration.

In further embodiments, the polypeptide ligand comprises a polypeptide linked to a molecular scaffold at n attachment points, wherein said polypeptide is cyclised and forms n separate loops subtended between said n attachment points on the molecular scaffold, wherein n is greater than or equal to 2.

The polypeptide is preferably cyclised by N- to C-terminal fusion, and can be cyclised before or after attachment to the molecular scaffold. Attachment before cyclisation is preferred.

Several methods are known in the art for peptide cyclisation. For example, the polypeptide is cyclised by N—C crosslinking, using a crosslinking agent such as EDC.

In another embodiment, the peptide can be designed to comprise a protected $N^\alpha$ or $C^\alpha$ derivatised amino acid, and cyclised by deprotection of the protected $N^\alpha$ or $C^\alpha$ derivatised amino acid to couple said amino acid to the opposite terminus of the polypeptide.

In a preferred embodiment, the polypeptide is cyclised by enzymatic means.

For example, the enzyme is a transglutaminase, for instance a microbial transglutaminase, such as *Streptomyces mobaraensis* transglutaminase. In order to take advantage of enzymatic cyclisation, it may be necessary to incorporate an N- and/or C-terminal substrate sequence for the enzyme in the polypeptide. Some or all of the substrate sequence(s) can be eliminated during the enzymatic reaction, meaning that the cyclised polypeptide may not comprise the substrate sequences in its final configuration.

DETAILED DESCRIPTION OF THE INVENTION

Figure 1:
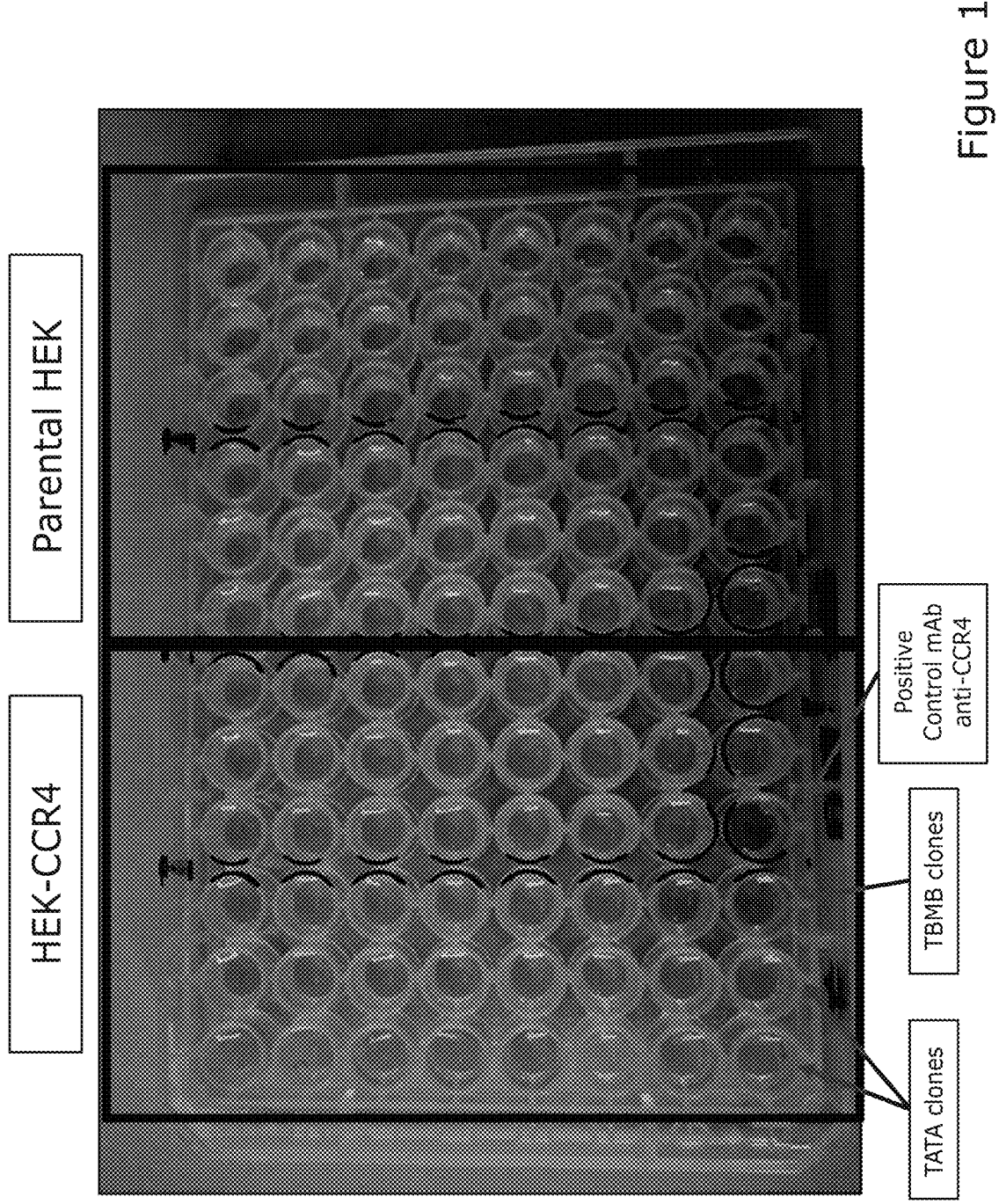
FIG. 1 shows an assay indicating the presence of peptides which bind CCR4, on selection against positive (CCR4-expressing) and negative cells.
Figure 2:
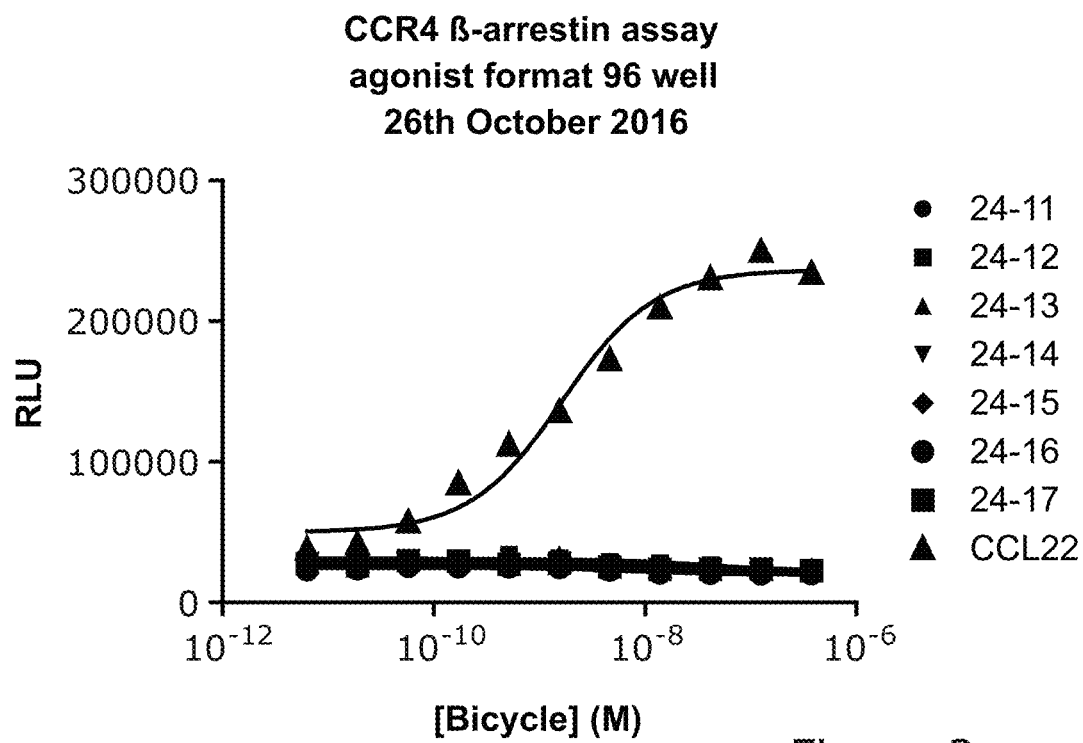
FIG. 2 illustrates the results of a beta-arrestin assay for CCR4 agonist activity in selected peptides.
Figure 3:
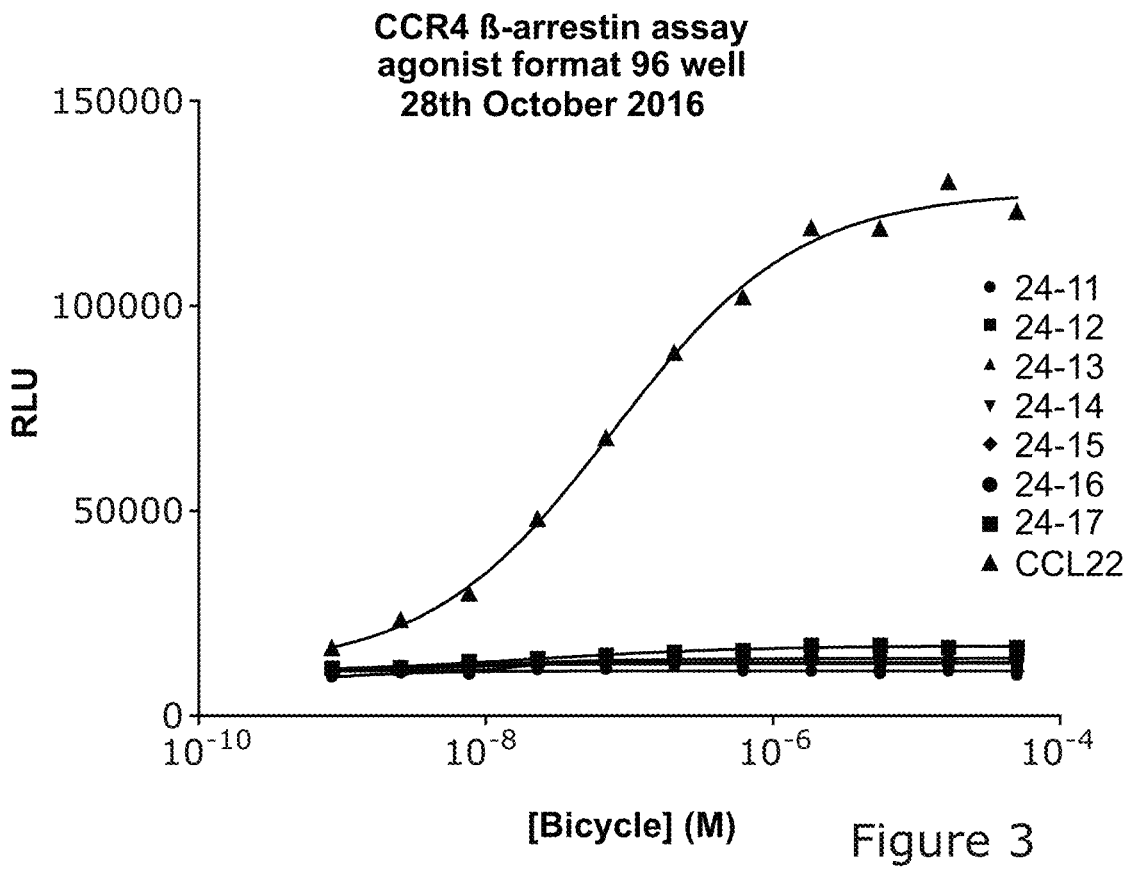
FIG. 3 illustrates the results of a beta-arrestin assay for CCR4 agonist activity in selected peptides at higher peptide concentrations.
Figure 4:
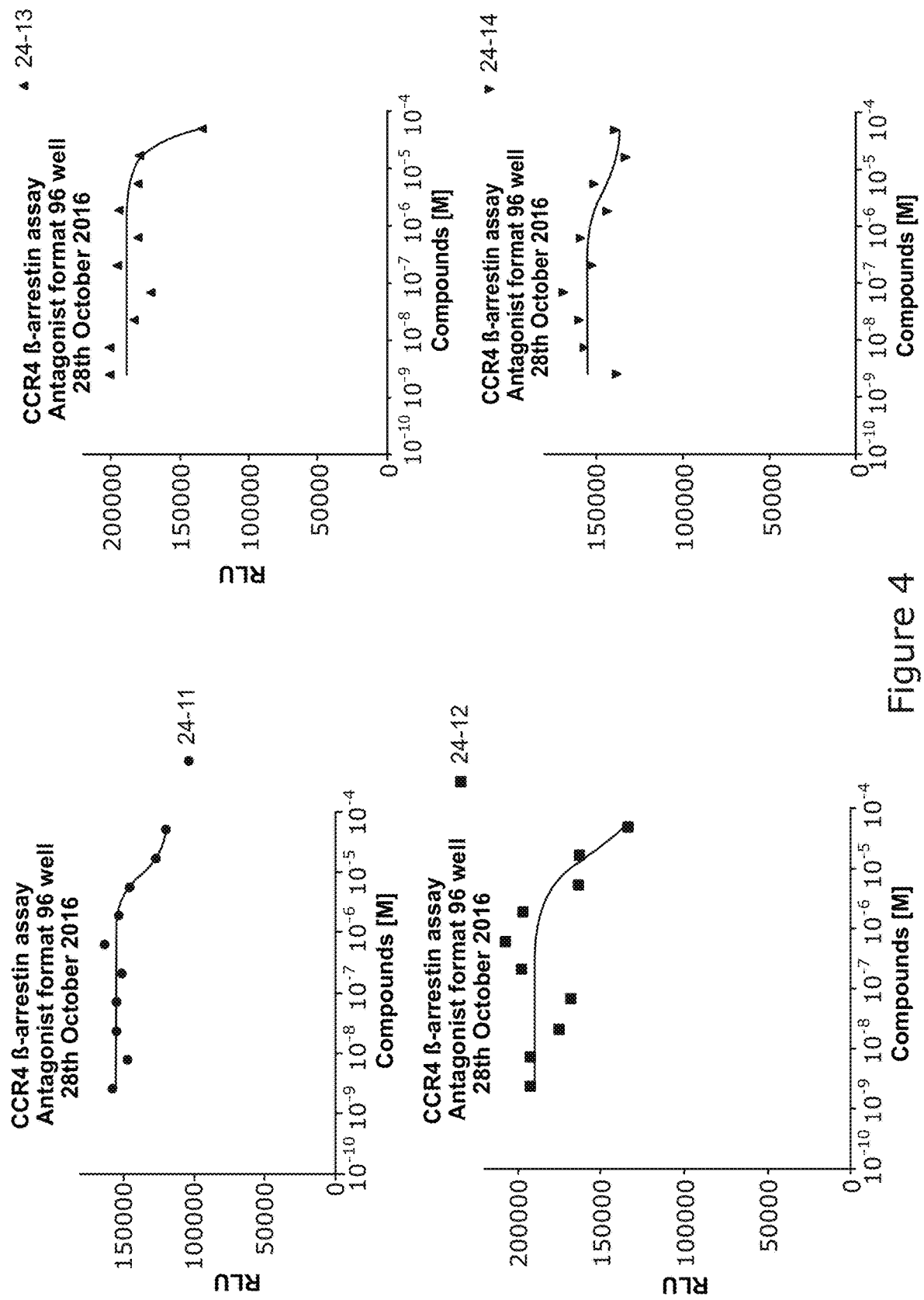
FIG. 4 illustrates the results of a beta-arrestin assay for CCR4 antagonist activity in selected peptides.
Figure 4:
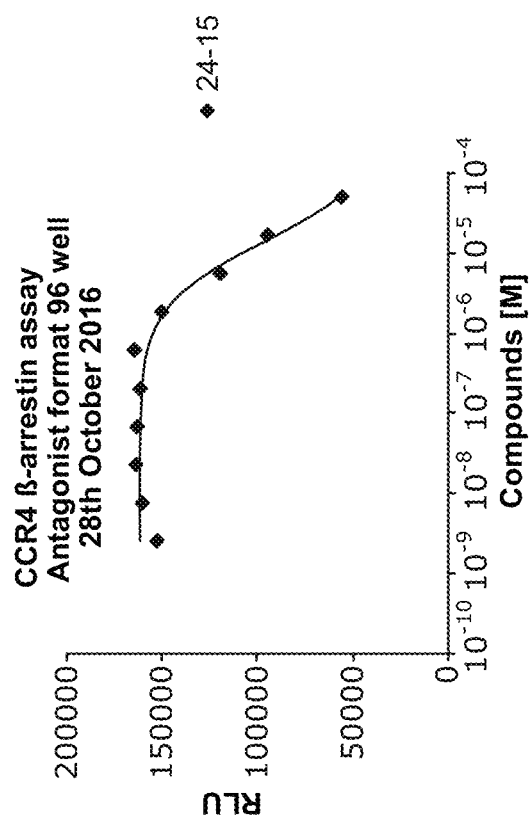
Figure 4:
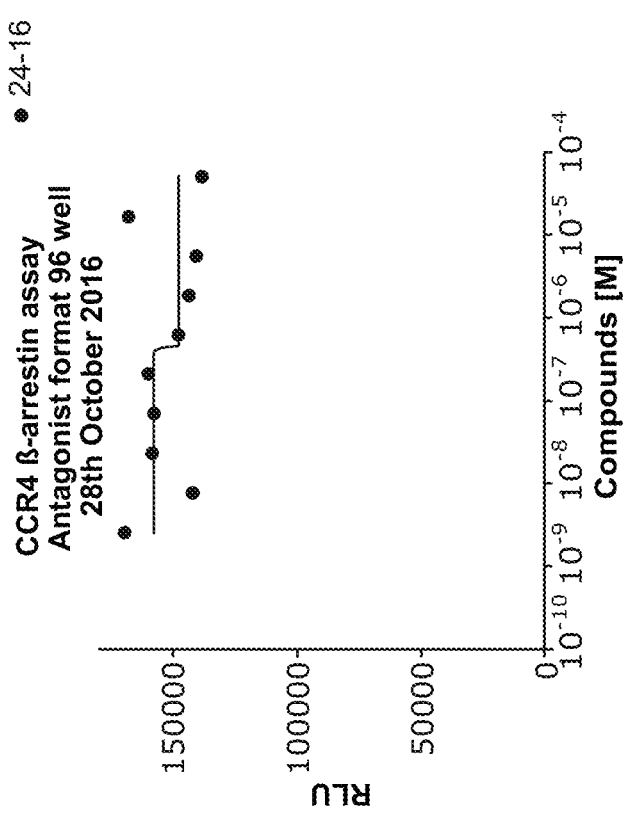
Figure 5:
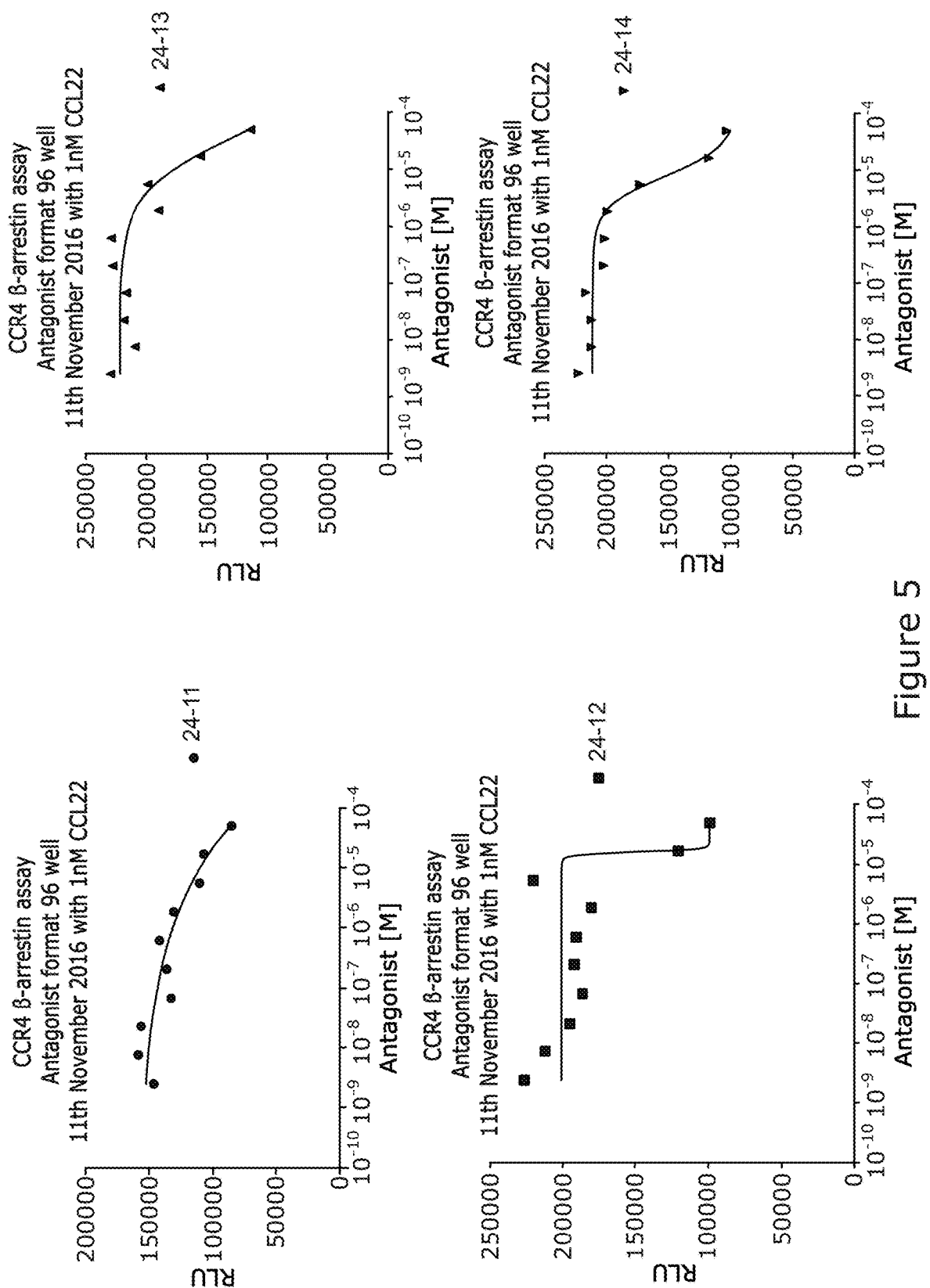
FIG. 5 illustrates the results of a beta-arrestin assay for CCR4 antagonist activity in selected peptides at lower ligand concentrations.
Figure 5:
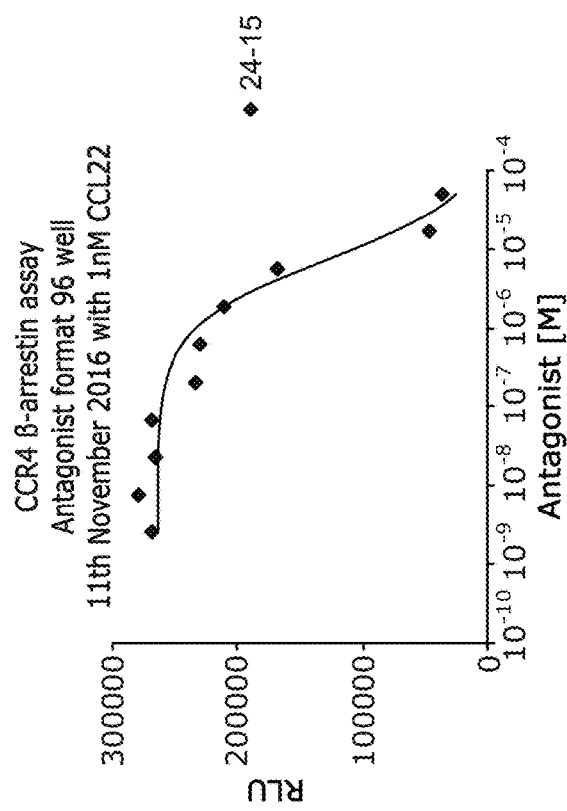
Figure 5:
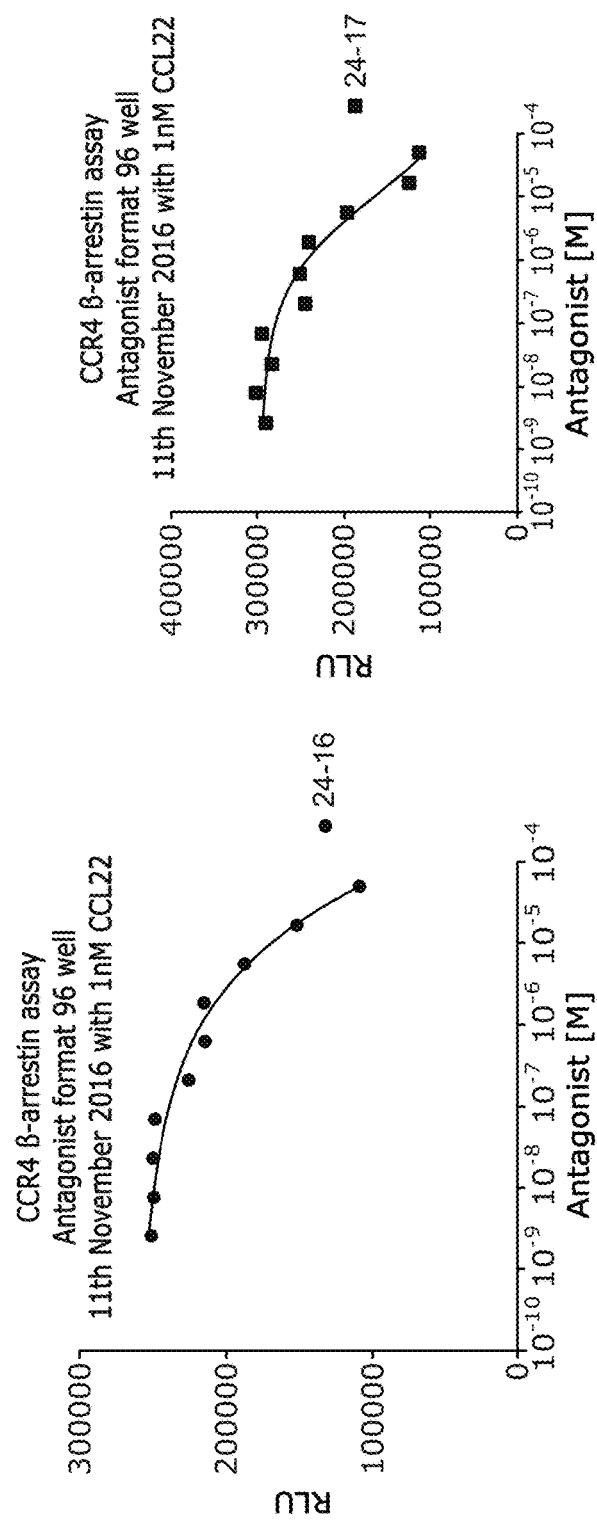
Figure 6A:
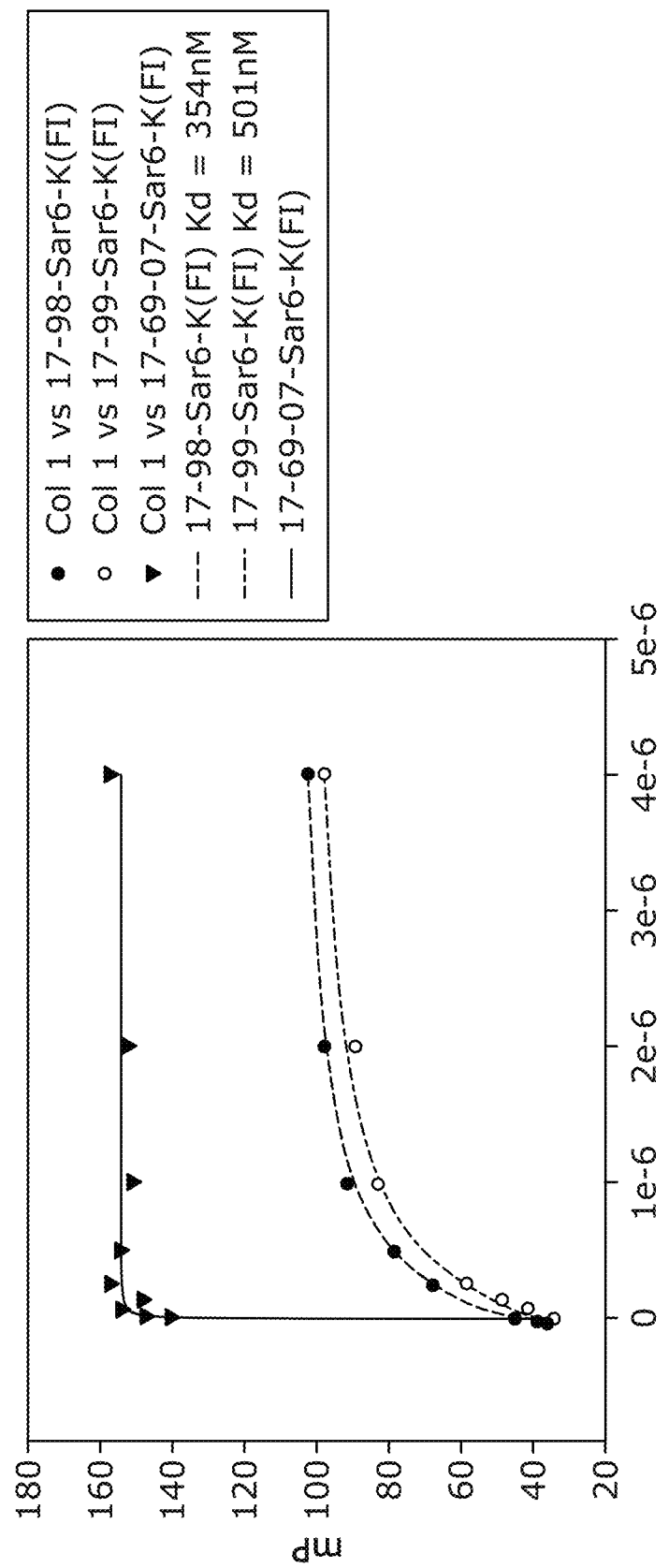
FIG. 6 illustrates an analysis of MT-MMP binding ligands. A: MMP-14 FP direct binding in cell-based selections; 1 nM tracer, 60 min data. 17-98-Sar6-k(Fl)-and-17-99-Sar6-k(Fl)-bind with Kds of 354 nM and 501 nM respectively. B: competition binding with several combinations of peptides, both fluorescein-labelled or native, from soluble and cell based selections.
Figure 6B:
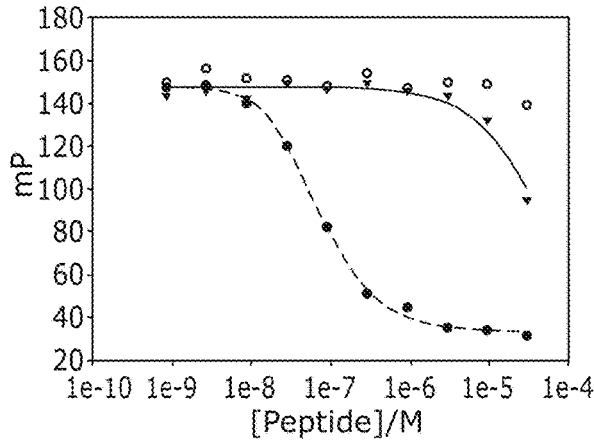
Figure 6B:
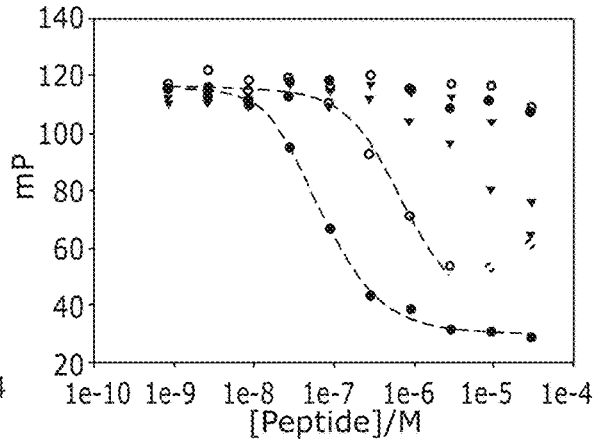
Figure 6B:
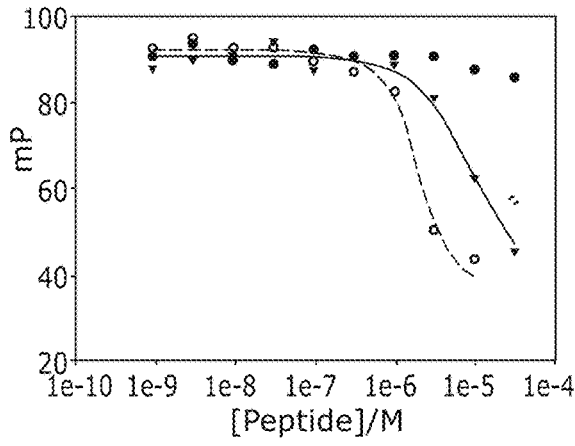
Figure 6B:
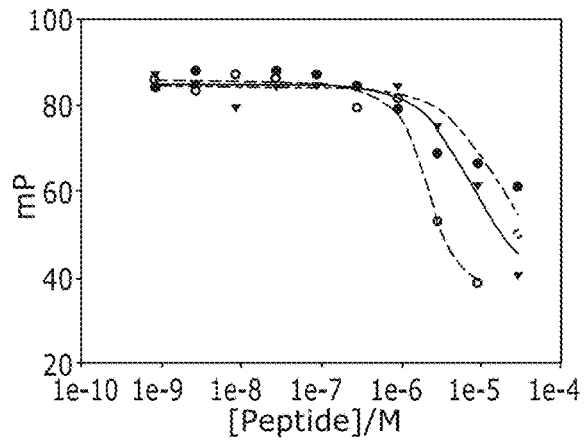

Unless defined otherwise, all technical and scientific terms used herein have the same meaning as commonly understood by those of ordinary skill in the art, such as in the arts of peptide chemistry, cell culture and phage display, nucleic acid chemistry and biochemistry.

Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, NY; Ausubel et al., Short Protocols in Molecular Biology (1999) $4^{th}$ ed., John Wiley & Sons, Inc.), which are incorporated herein by reference.

A (poly)peptide ligand or (poly)peptide conjugate, as referred to herein, refers to a polypeptide covalently bound to a molecular scaffold. Typically, such polypeptides comprise two or more reactive groups which are capable of forming covalent bonds to the scaffold, and a sequence subtended between said reactive groups which is referred to as the loop sequence, since it forms a loop when the peptide is bound to the scaffold. In the present case, the polypeptides comprise at least three reactive groups, and form at least two loops on the scaffold.

The reactive groups are groups capable of forming a covalent bond with the molecular scaffold. Typically, the reactive groups are present on amino acid side chains on the peptide. Examples are amino-containing groups such as cysteine, lysine, selenocysteine, serine, L-2, 3-diaminopropionic acid and N-beta-alkyl-L-2, 3-diaminopropionic acid.

Specificity, in the context herein, refers to the ability of a ligand to bind or otherwise interact with its cognate target to the exclusion of entities which are similar to the target. For example, specificity can refer to the ability of a ligand to inhibit the interaction of a human enzyme, but not a homologous enzyme from a different species. Using the approach described herein, specificity can be modulated, that is increased or decreased, so as to make the ligands more or less able to interact with homologues or paralogues of the intended target. Specificity is not intended to be synonymous with activity, affinity or avidity, and the potency of the action of a ligand on its target (such as, for example, binding affinity or level of inhibition) are not necessarily related to its specificity.

Binding activity, as used herein, refers to quantitative binding measurements taken from binding assays, for example as described herein. Therefore, binding activity refers to the amount of peptide ligand which is bound at a given target concentration.

Multispecificity is the ability to bind to two or more targets. Typically, binding peptides are capable of binding to a single target, such as an epitope in the case of an antibody, due to their conformational properties. However, peptides can be developed which can bind to two or more targets; dual specific antibodies, for example. In the present invention, the peptide ligands can be capable of binding to two or more targets and are therefore be multispecific. Preferably, they bind to two targets, and are dual specific. The binding may be independent, which would mean that the binding sites for the targets on the peptide are not structurally hindered by the binding of one or other of the targets. In this case both targets can be bound independently. More generally it is expected that the binding of one target will at least partially impede the binding of the other.

A target is a molecule or part thereof to which the peptide ligands bind or otherwise interact with. Although binding is seen as a prerequisite to activity of most kinds, and may be an activity in itself, other activities are envisaged. Thus, the present invention does not require the measurement of binding directly or indirectly.

The molecular scaffold is any molecule which is able to connect the peptide at multiple points to impart one or more structural features to the peptide. It is not a cross-linker, in that it does not merely replace a disulphide bond; instead, it provides two or more attachment points for the peptide. Preferably, the molecular scaffold comprises at least three attachment points for the peptide, referred to as scaffold reactive groups. These groups are capable of reacting to the reactive groups on the peptide to form a covalent bond. Preferred structures for molecular scaffolds are described below.

Screening for binding activity (or any other desired activity) is conducted according to methods well known in the art, for instance from phage display technology. For example, targets immobilised to a solid phase can be used to identify and isolate binding members of a repertoire. Screening allows selection of members of a repertoire according to desired characteristics.

The term library refers to a mixture of heterogeneous polypeptides or nucleic acids. The library is composed of members, which are not identical. To this extent, library is synonymous with repertoire. Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. Preferably, each individual organism or cell contains only one or a limited number of library members.

In one embodiment, the nucleic acids are incorporated into expression vectors, in order to allow expression of the polypeptides encoded by the nucleic acids. In a preferred aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

In one embodiment, a library of nucleic acids encodes a repertoire of polypeptides. Each nucleic acid member of the library preferably has a sequence related to one or more other members of the library. By related sequence is meant an amino acid sequence having at least 50% identity, for example at least 60% identity, for example at least 70% identity, for example at least 80% identity, for example at least 90% identity, for example at least 95% identity, for example at least 98% identity, for example at least 99% identity to at least one other member of the library. Identity can be judged across a contiguous segment of at least 3 amino acids, for example at least 4, 5, 6, 7, 8, 9 or 10 amino acids, for example least 12 amino acids, for example least 14 amino acids, for example least 16 amino acids, for example least 17 amino acids or the full length of the reference sequence.

A repertoire is a collection of variants, in this case polypeptide variants, which differ in their sequence. Typically, the location and nature of the reactive groups will not vary, but the sequences forming the loops between them can be randomised. Repertoires differ in size, but should be considered to comprise at least $10^2$ members. Repertoires of $10^{11}$ or more members can be constructed.

(1) (i) Molecular Scaffold

Molecular scaffolds are described in, for example, WO2009098450 and references cited therein, particularly WO2004077062 and WO2006078161.

The molecular scaffold is any molecule which is able to connect the peptide at multiple points to impart one or more structural features to the peptide. Preferably, the molecular scaffold comprises at least three attachment points for the peptide, referred to as scaffold reactive groups. These groups are capable of reacting with the cysteine residues ($C_i$, $C_{ii}$ and $C_{iii}$) on the peptide to form a covalent bond. They do not merely form a disulphide bond, which is subject to reductive cleavage and concomitant disintegration of the molecule, but form stable, covalent thioether linkages. Preferred structures for molecular scaffolds are described below.

The compounds of the invention thus comprise, consist essentially of, or consist of, the peptide covalently bound to a molecular scaffold. The term "scaffold" or "molecular scaffold" herein refers to a chemical moiety that is bonded to the peptide at the alkylamino linkages and thioether linkage in the compounds of the invention. The term "scaffold molecule" or "molecular scaffold molecule" herein refers to a molecule that is capable of being reacted with a peptide or peptide ligand to form the derivatives of the invention having alkylamino and thioether bonds. Thus, the scaffold molecule has the same structure as the scaffold moiety except that respective reactive groups (such as leaving groups) of the molecule are replaced by alkylamino and thioether bonds to the peptide in the scaffold moiety.

The molecular scaffold molecule is any molecule which is able to connect the peptide at multiple points to form the thioether and alkylamino bonds to the peptide. It is not a cross-linker, in that it does not normally link two peptides; instead, it provides two or more attachment points for a single peptide. The molecular scaffold molecule comprises at least three attachment points for the peptide, referred to as scaffold reactive groups. These groups are capable of reacting with —SH and amino groups on the peptide to form the thioether and alkylamino linkages. Thus, the molecular scaffold represents the scaffold moiety up to but not including the thioether and alkylamino linkages in the conjugates of the invention. The scaffold molecule has the structure of the scaffold, but with reactive groups at the locations of the thioether and alkylamino bonds in the conjugate of the invention.

Suitably, the scaffold comprises, consists essentially of, or consists of a (hetero)aromatic or (hetero)alicyclic moiety.

As used herein, "(hetero)aryl" is meant to include aromatic rings, for example, aromatic rings having from 4 to 12 members, such as phenyl rings. These aromatic rings can optionally contain one or more heteroatoms (e.g., one or more of N, O, S, and P), such as thienyl rings, pyridyl rings, and furanyl rings. The aromatic rings can be optionally substituted. "(hetero)aryl" is also meant to include aromatic rings to which are fused one or more other aryl rings or non-aryl rings. For example, naphthyl groups, indole groups, thienothienyl groups, dithienothienyl, and 5,6,7,8-tetrahydro-2-naphthyl groups (each of which can be optionally substituted) are aryl groups for the purposes of the present application. As indicated above, the aryl rings can be optionally substituted. Suitable substituents include alkyl groups (which can optionally be substituted), other aryl groups (which may themselves be substituted), heterocyclic rings (saturated or unsaturated), alkoxy groups (which is meant to include aryloxy groups (e.g., phenoxy groups)), hydroxy groups, aldehyde groups, nitro groups, amine groups (e.g., unsubstituted, or mono- or di-substituted with aryl or alkyl groups), carboxylic acid groups, carboxylic acid derivatives (e.g., carboxylic acid esters, amides, etc.), halogen atoms (e.g., Cl, Br, and I), and the like.

As used herein, "(hetero)alicyclic" refers to a homocyclic or heterocyclic saturated ring. The ring can be unsubstituted, or it can be substituted with one or more substituents. The substituents can be saturated or unsaturated, aromatic or nonaromatic, and examples of suitable substituents include those recited above in the discussion relating to substituents on alkyl and aryl groups. Furthermore, two or more ring substituents can combine to form another ring, so that "ring", as used herein, is meant to include fused ring systems.

Suitably, the scaffold comprises a tris-substituted (hetero) aromatic or (hetero)alicyclic moiety, for example a tris-methylene substituted (hetero)aromatic or (hetero)alicyclic moiety. The (hetero)aromatic or (hetero)alicyclic moiety is suitably a six-membered ring structure, preferably tris-substituted such that the scaffold has a 3-fold symmetry axis.

In embodiments, the scaffold is a tris-methylene (hetero) aryl moiety, for example a 1,3,5-tris methylene benzene moiety. In these embodiments, the corresponding scaffold molecule suitably has a leaving group on the methylene carbons. The methylene group then forms the $R_1$ moiety of the alkylamino linkage as defined herein. In these methylene-substituted (hetero)aromatic compounds, the electrons of the aromatic ring can stabilize the transition state during nucleophilic substitution. Thus, for example, benzyl halides are 100-1000 times more reactive towards nucleophilic substitution than alkyl halides that are not connected to a (hetero)aromatic group.

In these embodiments the scaffold and scaffold molecule have the general formula:

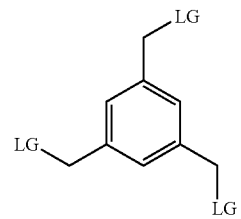

Where LG represents a leaving group as described further below for the scaffold molecule, or LG (including the adjacent methylene group forming the $R_1$ moiety of the alkylamino group) represents the alkylamino linkage to the peptide in the conjugates of the invention.

In embodiments, the group LG above may be a halogen such as, but not limited to, a bromine atom, in which case the scaffold molecule is 1,3,5-Tris(bromomethyl)benzene (TBMB). Another suitable molecular scaffold molecule is 2,4,6-tris(bromomethyl) mesitylene. It is similar to 1,3,5-tris(bromomethyl) benzene but contains additionally three methyl groups attached to the benzene ring. In the case of this scaffold, the additional methyl groups may form further contacts with the peptide and hence add additional structural constraint. Thus, a different diversity range is achieved than with 1,3,5-Tris(bromomethyl)benzene.

Another preferred molecule for forming the scaffold for reaction with the peptide by nucleophilic substitution is 1,3,5-tris(bromoacetamido)benzene (TBAB):

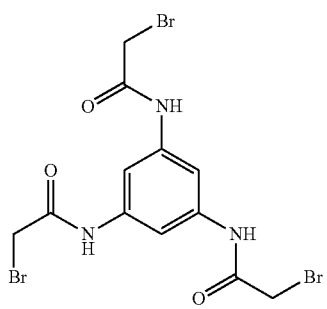 [SMILES: O=C(CBr)Nc1cc(NC(=O)CBr)cc(NC(=O)CBr)c1]

In other embodiments the molecular scaffold may have a tetrahedral geometry such that reaction of four functional groups of the encoded peptide with the molecular scaffold generates not more than two product isomers. Other geometries are also possible; indeed, an almost infinite number of scaffold geometries is possible, leading to greater possibilities for peptide ligand diversification.

The peptides used to form the ligands of the invention can comprise Dap or N-AlkDap residues for forming alkylamino linkages to the scaffold. The structure of diaminopropionic acid is analogous to and isosteric that of cysteine that has been used to form thioether bonds to the scaffold in the prior art, with replacement of the terminal —SH group of cysteine by —NH$_2$:

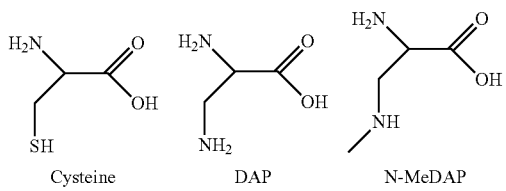

The term "alkylamino" is used herein in its normal chemical sense to denote a linkage consisting of NH or N(R$_3$) bonded to two carbon atoms, wherein the carbon atoms are independently selected from alkyl, alkylene, or aryl carbon atoms and R$_3$ is an alkyl group. Suitably, the alkylamino linkages of the invention comprise an NH moiety bonded to two saturated carbon atoms, most suitably methylene (—CH$_2$—) carbon atoms. The alkylamino linkages useful in the invention have general formula:

Wherein:
S represents the scaffold core, e.g. a (hetero)aromatic or (hetero)alicyclic ring as explained further below;
R$_1$ is C1 to C3 alkylene groups, suitably methylene or ethylene groups, and most suitably methylene (CH$_2$);
R$_2$ is the methylene group of the Dap or N-AlkDap side chain
R$_3$ is C1-4 alkyl including branched alkyl and cycloalkyl, for example methyl, or H; and
P represents the peptide backbone, i.e. the R$_2$ moiety of the above linkage is linked to the carbon atom in the peptide backbone adjacent to a carboxylic carbon of the Dap or N-AlkDap residue.

(ii) Polypeptide

The reactive groups of the polypeptides can be provided by side chains of natural or non-natural amino acids. The reactive groups of the polypeptides can be selected from thiol groups, amino groups, carboxyl groups, guanidinium groups, phenolic groups or hydroxyl groups. The reactive groups of the polypeptides can be selected from azide, keto-carbonyl, alkyne, vinyl, or aryl halide groups. The reactive groups of the polypeptides for linking to a molecular scaffold can be the amino or carboxy termini of the polypeptide.

In some embodiments each of the reactive groups of the polypeptide for linking to a molecular scaffold are of the same type. For example, each reactive group may be a cysteine residue. Further details are provided in WO2009098450.

In some embodiments the reactive groups for linking to a molecular scaffold may comprise two or more different types, or may comprise three or more different types. For example, the reactive groups may comprise two cysteine residues and one lysine residue, or may comprise one cysteine residue, one lysine residue and one N-terminal amine.

Cysteine can be employed because it has the advantage that its reactivity is most different from all other amino acids. Scaffold reactive groups that could be used on the molecular scaffold to react with thiol groups of cysteines are alkyl halides (or also named halogenoalkanes or haloalkanes). Examples are bromomethylbenzene (the scaffold reactive group exemplified by TBMB) or iodoacetamide. Other scaffold reactive groups that are used to couple selectively compounds to cysteines in proteins are maleimides. Examples of maleimides which may be used as molecular scaffolds in the invention include: tris-(2-maleimidoethyl)amine, tris-(2-maleimidoethyl)benzene, tris-(maleimido)benzene. Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Lysines (and primary amines of the N-terminus of peptides) are also suited as reactive groups to modify peptides on phage by linking to a molecular scaffold. However, they are more abundant in phage proteins than cysteines and there is a higher risk that phage particles might become cross-linked or that they might lose their infectivity. Nevertheless, it has been found that lysines are especially useful in intramolecular reactions (e.g. when a molecular scaffold is already linked to the phage peptide) to form a second or consecutive linkage with the molecular scaffold. In this case the molecular scaffold reacts preferentially with lysines of the displayed peptide (in particular lysines that are in close proximity). Scaffold reactive groups that react selectively with primary amines are succinimides, aldehydes or alkyl halides. In the bromomethyl group that is used in a number of the accompanying examples, the electrons of the benzene ring can stabilize the cationic transition state. This particular aryl halide is therefore 100-1000 times more reactive than alkyl halides. Examples of succinimides for use as molecular scaffold include tris-(succinimidyl aminotriacetate), 1,3,5-Benzenetriacetic acid. Examples of aldehydes for use as molecular scaffold include Triformylmethane. Examples of alkyl halides for use as molecular scaffold include 1,3,5-Tris(bromomethyl)-2,4,6-trimethylbenzene, 1,3,5-Tris(bromomethyl) benzene, 1,3,5-Tris(bromomethyl)-2,4,6-triethylbenzene.

The amino acids with reactive groups for linking to a molecular scaffold may be located at any suitable positions within the polypeptide. In order to influence the particular structures or loops created, the positions of the amino acids having the reactive groups may be varied by the skilled operator, e.g. by manipulation of the nucleic acid encoding the polypeptide in order to mutate the polypeptide produced. By such means, loop length can be manipulated in accordance with the present teaching.

For example, the polypeptide can comprise the sequence $AC(X)_nC(X)_mCG$, wherein X stands for a random natural amino acid, A for alanine, C for cysteine and G for glycine and n and m, which may be the same or different, are numbers between 2 and 15, and in embodiments may be between 2 and 10, 2 and 9, 2 and 7 or 2 and 6.

(iii) Reactive Groups of the Polypeptide

The molecular scaffold of the invention may be bonded to the polypeptide via functional or reactive groups on the polypeptide. These are typically formed from the side chains of particular amino acids found in the polypeptide polymer. Such reactive groups may be a cysteine side chain, a lysine side chain, or an N-terminal amine group or any other suitable reactive group. Again, details may be found in WO2009098450.

Examples of reactive groups of natural amino acids are the thiol group of cysteine, the amino group of lysine, the carboxyl group of aspartate or glutamate, the guanidinium group of arginine, the phenolic group of tyrosine or the hydroxyl group of serine. Non-natural amino acids can provide a wide range of reactive groups including an azide, a keto-carbonyl, an alkyne, a vinyl, or an aryl halide group. The amino and carboxyl group of the termini of the polypeptide can also serve as reactive groups to form covalent bonds to a molecular scaffold/molecular core.

The polypeptides of the invention contain at least three reactive groups. Said polypeptides can also contain four or more reactive groups. The more reactive groups are used, the more loops can be formed in the molecular scaffold.

In a preferred embodiment, polypeptides with three reactive groups are generated. Reaction of said polypeptides with a molecular scaffold/molecular core having a three-fold rotational symmetry generates a single product isomer. The generation of a single product isomer is favourable for several reasons. The nucleic acids of the compound libraries encode only the primary sequences of the polypeptide but not the isomeric state of the molecules that are formed upon reaction of the polypeptide with the molecular core. If only one product isomer can be formed, the assignment of the nucleic acid to the product isomer is clearly defined. If multiple product isomers are formed, the nucleic acid cannot give information about the nature of the product isomer that was isolated in a screening or selection process. The formation of a single product isomer is also advantageous if a specific member of a library of the invention is synthesized. In this case, the chemical reaction of the polypeptide with the molecular scaffold yields a single product isomer rather than a mixture of isomers.

In another embodiment of the invention, polypeptides with four reactive groups are generated. Reaction of said polypeptides with a molecular scaffold/molecular core having a tetrahedral symmetry generates two product isomers. Even though the two different product isomers are encoded by one and the same nucleic acid, the isomeric nature of the isolated isomer can be determined by chemically synthesizing both isomers, separating the two isomers and testing both isomers for binding to a target ligand.

In one embodiment of the invention, at least one of the reactive groups of the polypeptides is orthogonal to the remaining reactive groups. The use of orthogonal reactive groups allows the directing of said orthogonal reactive groups to specific sites of the molecular core. Linking strategies involving orthogonal reactive groups may be used to limit the number of product isomers formed. In other words, by choosing distinct or different reactive groups for one or more of the at least three bonds to those chosen for the remainder of the at least three bonds, a particular order of bonding or directing of specific reactive groups of the polypeptide to specific positions on the molecular scaffold may be usefully achieved.

In another embodiment, the reactive groups of the polypeptide of the invention are reacted with molecular linkers wherein said linkers are capable to react with a molecular scaffold so that the linker will intervene between the molecular scaffold and the polypeptide in the final bonded state.

In some embodiments, amino acids of the members of the libraries or sets of polypeptides can be replaced by any natural or non-natural amino acid. Excluded from these exchangeable amino acids are the ones harbouring functional groups for cross-linking the polypeptides to a molecular core, such that the loop sequences alone are exchangeable.

The exchangeable polypeptide sequences have either random sequences, constant sequences or sequences with random and constant amino acids. The amino acids with reactive groups are either located in defined positions within the polypeptide, since the position of these amino acids determines loop size.

In one embodiment, an polypeptide with three reactive groups has the sequence $(X)_lY(X)_mY(X)_nY(X)_o$, wherein Y represents an amino acid with a reactive group, X represents a random amino acid, m and n are numbers between 2 and 9 defining the length of intervening polypeptide segments, which may be the same or different, and l and o are numbers between 0 and 20 defining the length of flanking polypeptide segments.

Alternatives to thiol-mediated conjugations can be used to attach the molecular scaffold to the peptide via covalent interactions. Alternatively these techniques may be used in modification or attachment of further moieties (such as small molecules of interest which are distinct from the molecular scaffold) to the polypeptide after they have been selected or isolated according to the present invention—in this embodiment then clearly the attachment need not be covalent and may embrace non-covalent attachment. These methods may be used instead of (or in combination with) the thiol mediated methods by producing phage that display proteins and peptides bearing unnatural amino acids with the requisite chemical reactive groups, in combination small molecules that bear the complementary reactive group, or by incorporating the unnatural amino acids into a chemically or recombinantly synthesised polypeptide when the molecule is being made after the selection/isolation phase. Further details can be found in WO2009098450 or Heinis, et al., *Nat Chem Biol* 2009, 5 (7), 502-7.

(iv) Combination of Loops to Form Multispecific Molecules

Loops from peptide ligands, or repertoires of peptide ligands, are advantageously combined by sequencing and de novo synthesis of a polypeptide incorporating the combined loops. Alternatively, nucleic acids encoding such polypeptides can be synthesised.

Where repertoires are to be combined, particularly single loop repertoires, the nucleic acids encoding the repertoires are advantageously digested and re-ligated, to form a novel repertoire having different combinations of loops from the constituent repertoires. Phage vectors can include polylinkers and other sites for restriction enzymes which can provide unique points for cutting and relegation the vectors, to create the desired multispecific peptide ligands. Methods for manipulating phage libraries are well known in respect of antibodies, and can be applied in the present case also.

(v) Attachment of Effector Groups and Functional Groups

Effector and/or functional groups can be attached, for example, to the N or C termini of the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further preferred embodiment of this aspect of the invention, an effector group according to the present invention is an Fc region of an IgG molecule. Advantageously, a peptide ligand-effector group according to the present invention comprises or consists of a peptide ligand Fc fusion having a $t\beta$ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a $t\beta$ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of *Drosophila* (Antennapedia), e.g. as described in Chen and Harrison, Biochemical Society Transactions (2007) Volume 35, part 4, p 821 "Cell-penetrating peptides in drug development: enabling intracellular targets" and "Intracellular delivery of large molecules and small peptides by cell penetrating peptides" by Gupta et al. in Advanced Drug Discovery Reviews (2004) Volume 57 9637. Examples of short peptides which have been shown to be efficient at translocation through plasma membranes include the 16 amino acid penetratin peptide from *Drosophila* Antennapedia protein (Derossi et al (1994) J Biol. Chem. Volume 269 p 10444 "The third helix of the Antennapedia homeodomain translocates through biological membranes"), the 18 amino acid 'model amphipathic peptide' (Oehlke et al (1998) Biochim Biophys Acts Volume 1414 p 127 "Cellular uptake of an alpha-helical amphipathic model peptide with the potential to deliver polar compounds into the cell interior non-endocytically") and arginine rich regions of the HIV TAT protein. Non peptidic approaches include the use of small molecule mimics or SMOCs that can be easily attached to biomolecules (Okuyama et al (2007) Nature Methods Volume 4 p 153 'Small-molecule mimics of an a-helix for efficient transport of proteins into cells'. Other chemical strategies to add guanidinium groups to molecules also enhance cell penetration (Elson-Scwab et al (2007) J Biol Chem Volume 282 p 13585 "Guanidinylated Neomcyin Delivers Large Bioactive Cargo into cells through a heparin Sulphate Dependent Pathway"). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half life of the peptide ligand in vivo may be used.

RGD peptides, which bind to integrins which are present on many cells, may also be incorporated.

In one embodiment, a peptide ligand-effector group according to the invention has a $t\beta$ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a $t\beta$ half life in the range 12 to 60 hours. In a further embodiment, it will have a t half-life of a day or more. In a further embodiment still, it will be in the range 12 to 26 hours.

Functional groups include drugs, such as cytotoxic agents for cancer therapy. These include Alkylating agents such as Cisplatin and carboplatin, as well as oxaliplatin, mechlorethamine, cyclophosphamide, chlorambucil, ifosfamide; Anti-metabolites including purine analogs azathioprine and mercaptopurine)) or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include Antitumour antibiotics which include the immunosuppressant dactinomycin (which is used in kidney transplantations), doxorubicin, epirubicin, bleomycin and others.

Possible effector groups also include enzymes, for instance such as carboxypeptidase G2 for use in enzyme/ prodrug therapy, where the peptide ligand replaces antibodies in ADEPT.

(vi) Peptide Modification

To develop the bicyclic peptides (Bicycles; peptides conjugated to molecular scaffolds) into a suitable drug-like molecule, whether that be for injection, inhalation, nasal, ocular, oral or topical administration, a number of properties need considered. The following at least need to be designed into a given lead Bicycle:

protease stability, whether this concerns Bicycle stability to plasma proteases, epithelial ("membrane-anchored") proteases, gastric and intestinal proteases, lung surface proteases, intracellular proteases and the like. Protease stability should be maintained between different species such that a Bicycle lead candidate can be developed in animal models as well as administered with confidence to humans.

replacement of oxidation-sensitive residues, such as tryptophan and methionine with oxidation-resistant analogues in order to improve the pharmaceutical stability profile of the molecule a desirable solubility profile, which is a function of the proportion of charged and hydrophilic versus hydrophobic residues, which is important for formulation and absorption purposes correct balance of charged versus hydrophobic residues, as hydrophobic residues influence the degree of plasma protein binding and thus the concentration of the free available fraction in plasma, while charged residues (in particular arginines) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic residues may reduce irritation at the injection site (were the peptide drug administered subcutaneously).

a tailored half-life, depending on the clinical indication and treatment regimen. It may be prudent to develop an unmodified molecule for short exposure in an acute illness management setting, or develop a bicyclic peptide with chemical modifications that enhance the plasma half-life, and hence be optimal for the management of more chronic disease states.

Approaches to stabilise therapeutic peptide candidates against proteolytic degradation are numerous, and overlap with the peptidomimetics field (for reviews see Gentilucci et al, Curr. Pharmaceutical Design, (2010), 16, 3185-203, and Nestor et al, Curr. Medicinal Chem (2009), 16, 4399-418).

These include

Cyclisation of peptide

N- and C-terminal capping, usually N-terminal acetylation and C-terminal amidation.

Alanine scans, to reveal and potentially remove the proteolytic attack site(s).

D-amino acid replacement, to probe the steric requirements of the amino acid side chain, to increase proteolytic stability by steric hindrance and by a propensity of D-amino acids to stabilise β-turn conformations (Tugyi et al (2005) PNAS, 102(2), 413-418).

N-methyl/N-alkyl amino acid replacement, to impart proteolytic protection by direct modification of the scissile amide bond (Fiacco et al, Chembiochem. (2008), 9(14), 2200-3). N-methylation also has strong effect on the torsional angles of the peptide bond, and is believed to aid in cell penetration & oral availability (Biron et al (2008), Angew. Chem. Int. Ed., 47, 2595-99)

Incorporation of non-natural amino acids, i.e. by employing

Isosteric/isoelectronic side chains that are not recognised by proteases, yet have no effect on target potency Constrained amino acid side chains, such that proteolytic hydrolysis of the nearby peptide bond is conformationally and sterically impeded. In particular, these concern proline analogues, bulky side-chains, Cα-disubstituted derivatives (where the simplest derivative is Aib, $H_2N-C(CH_3)_2-COOH$), and cyclo amino acids, a simple derivative being amino-cyclopropylcarboxylic acid).

Peptide bond surrogates, and examples include

N-alkylation (see above, i.e. CO—NR)

Reduced peptide bonds ($CH_2$—NH—)

Peptoids (N-alkyl amino acids, NR—$CH_2$—CO)

Thio-amides (CS—NH)

Azapeptides (CO—NH—NR)

Trans-alkene (RHC=C—)

Retro-inverso (NH—CO)

Urea surrogates (NH—CO—NHR)

Peptide backbone length modulation i.e. $β^{2/3}$-amino acids, (NH—CR—$CH_2$—CO, NH—$CH_2$—CHR—CO), Substitutions on the alpha-carbon on amino acids, which constrains backbone conformations, the simplest derivative being Aminoisobutyric acid (Aib).

It should be explicitly noted that some of these modifications may also serve to deliberately improve the potency of the peptide against the target, or, for example to identify potent substitutes for the oxidation-sensitive amino acids (Trp and Met).

(vii) Cells

In accordance with the present invention, phage bearing peptide ligands are screened against cells which express the desired target. Cells should be selected for the ability to properly express the desired target at the cell surface in a correctly folded manner, such that the target is presented at the surface of the cell as it would be in vivo.

In the case of peptide ligands intended for therapeutic applications, mammalian cells are advantageously used. Cells can be selected which naturally express the desired target, or cells can be transformed with nucleic acid which encodes the desired target.

It is desirable to identify a cell type which is also available as a "negative" cell, which is identical as the cell expressing the target except in that it does not express the target. If the cell is transformed to express the target, then the negative cell can be an untransformed or mock-transformed cell. If the cell naturally expresses the target, then the negative cell can be a cell in which target expression is attenuated, for example using RNAi approaches. Alternatively, it can be a similar cell type which does not express the target.

Cells which can be transformed with desired targets include a variety of cell lines, such as HEK 293 cells, HeLa cells, U2OS cells, A549 cells, HT1080 cells, CAD cells, P19 cells, NIH 3T3 cells, L929 cells, N2a cells, CHO cells, MCF-7 cells, Y79 cells, SO—Rb50 cells, Hep G2 cells, DUKX-X11 cells, J558L cells and BHK cells. Insect cells such as Sf9, bacterial cells such as E. coli and yeast cells such as S. cerevisiae may also be transformed. As noted above, membrane preparations may be sused from these or other cells, as may artificial membranes and membrane bodies such as liposomes, virus-like particles, membrane envelopes, and the like.

(B) Repertoires, Sets and Groups of Polypeptide Ligands (i) Construction of Libraries Libraries intended for selection may be constructed using techniques known in the art, for example as set forth in WO2004/077062, or biological systems, including phage vector systems as described herein. Other vector systems are known in the art, and include other phage (for instance, phage lambda), bacterial plasmid expression vectors, eukaryotic cell-based expression vectors, including yeast vectors, and the like. For example, see WO2009098450 or Heinis, et al., Nat Chem Biol 2009, 5 (7), 502-7.

Non-biological systems such as those set forth in WO2004/077062 are based on conventional chemical screening approaches. They are simple, but lack the power of biological systems since it is impossible, or at least impracticably onerous, to screen large libraries of peptide ligands. However, they are useful where, for instance, only a small number of peptide ligands needs to be screened. Screening by such individual assays, however, may be time-consuming and the number of unique molecules that can be tested for binding to a specific target generally does not exceed $10^6$ chemical entities.

In contrast, biological screening or selection methods generally allow the sampling of a much larger number of different molecules. Thus biological methods can be used in application of the invention. In biological procedures, molecules are assayed in a single reaction vessel and the ones with favourable properties (i.e. binding) are physically separated from inactive molecules. Selection strategies are available that allow to generate and assay simultaneously more than $10^{13}$ individual compounds. Examples for powerful affinity selection techniques are phage display, ribosome display, mRNA display, yeast display, bacterial display or RNA/DNA aptamer methods. These biological in vitro selection methods have in common that ligand repertoires are encoded by DNA or RNA. They allow the propagation and the identification of selected ligands by sequencing. Phage display technology has for example been used for the isolation of antibodies with very high binding affinities to virtually any target.

When using a biological system, once a vector system is chosen and one or more nucleic acid sequences encoding polypeptides of interest are cloned into the library vector, one may generate diversity within the cloned molecules by undertaking mutagenesis prior to expression; alternatively, the encoded proteins may be expressed and selected before mutagenesis and additional rounds of selection are performed.

Mutagenesis of nucleic acid sequences encoding structurally optimised polypeptides is carried out by standard molecular methods. Of particular use is the polymerase chain reaction, or PCR, (Mullis and Faloona (1987) Methods Enzymol., 155: 335, herein incorporated by reference). PCR, which uses multiple cycles of DNA replication catalysed by a thermostable, DNA-dependent DNA polymerase to amplify the target sequence of interest, is well known in the art. The construction of various antibody libraries has been discussed in Winter et al. (1994) Ann. Rev. Immunology 12, 433-55, and references cited therein.

Alternatively, given the short chain lengths of the polypeptides according to the invention, the variants are preferably synthesised de novo and inserted into suitable expression vectors. Peptide synthesis can be carried out by standard techniques known in the art, as described above. Automated peptide synthesisers are widely available, such as the Applied Biosystems ABI 433 (Applied Biosystems, Foster City, CA, USA)

(ii) Genetically Encoded Diversity

In one embodiment, the polypeptides of interest are genetically encoded. This offers the advantage of enhanced diversity together with ease of handling. An example of a genetically polypeptide library is a mRNA display library. Another example is a replicable genetic display package (rgdp) library such as a phage display library. In one embodiment, the polypeptides of interest are genetically encoded as a phage display library. Thus, in one embodiment the complex of the invention comprises a replicable genetic display package (rgdp) such as a phage particle. In these embodiments, the nucleic acid can be comprised by the phage genome. In these embodiments, the polypeptide can be comprised by the phage coat.

In some embodiments, the invention may be used to produce a genetically encoded combinatorial library of polypeptides which are generated by translating a number of nucleic acids into corresponding polypeptides and linking molecules of said molecular scaffold to said polypeptides.

The genetically encoded combinatorial library of polypeptides may be generated by phage display, yeast display, ribosome display, bacterial display or mRNA display.

Techniques and methodology for performing phage display can be found in WO2009098450.

In one embodiment, screening may be performed by contacting a library, set or group of polypeptide ligands with a target and isolating one or more member(s) that bind to said target.

In another embodiment, individual members of said library, set or group are contacted with a target in a screen and members of said library that bind to said target are identified.

In another embodiment, members of said library, set or group are simultaneously contacted with a target and members that bind to said target are selected.

The target(s) may be a peptide, a protein, a polysaccharide, a lipid, a DNA or a RNA.

The target may be a receptor, a receptor ligand, an enzyme, a hormone or a cytokine.

The target may be a prokaryotic protein, a eukaryotic protein, or an archeal protein. More specifically the target ligand may be a mammalian protein or an insect protein or a bacterial protein or a fungal protein or a viral protein.

The target ligand may be an enzyme, such as a protease.

It should be noted that the invention also embraces polypeptide ligands isolated from a screen according to the invention. In one embodiment the screening method(s) of the invention further comprise the step of: manufacturing a quantity of the polypeptide isolated as capable of binding to said targets.

The invention also relates to peptide ligands having more than two loops. For example, tricyclic polypeptides joined to a molecular scaffold can be created by joining the N- and C-termini of a bicyclic polypeptide joined to a molecular scaffold according to the present invention. In this manner, the joined N and C termini create a third loop, making a tricyclic polypeptide. This embodiment need not be carried out on phage, but can be carried out on a polypeptide-molecular scaffold conjugate as described herein. Joining the N- and C-termini is a matter of routine peptide chemistry. In case any guidance is needed, the C-terminus may be activated and/or the N- and C-termini may be extended for example to add a cysteine to each end and then join them by disulphide bonding. Alternatively the joining may be accomplished by use of a linker region incorporated into the N/C termini. Alternatively the N and C termini may be joined by a conventional peptide bond. Alternatively any other suitable means for joining the N and C termini may be employed, for example N—C-cyclization could be done by standard techniques, for example as disclosed in Linde et al. Peptide Science 90, 671-682 (2008) "Structure-activity relationship and metabolic stability studies of backbone cyclization and N-methylation of melanocortin peptides", or as in Hess et al. J. Med. Chem. 51, 1026-1034 (2008) "backbone cyclic peptidomimetic melanocortin-4 receptor agonist as a novel orally administered drug lead for treating obesity". One advantage of such tricyclic molecules is the avoidance of proteolytic degradation of the free ends, in particular by exoprotease action. Another advantage of a tricyclic polypeptide of this nature is that the third loop may be utilised for generally applicable functions such as BSA binding, cell entry or transportation effects, tagging or any other such use. It will be noted that this third loop will not typically be available for selection (because it is not produced on the phage but only on the polypeptide-molecular scaffold conjugate) and so its use for other such biological functions still advantageously leaves both loops 1 and 2 for selection/creation of specificity.

(iii) Phage Purification

In accordance with the present invention, phage purification before reaction with the molecular scaffold is optional.

In the event that purification is desired, any suitable means for purification of the phage may be used. Standard techniques may be applied in the present invention. For example, phage may be purified by filtration or by precipitation such as PEG precipitation; phage particles may be produced and purified by polyethylene-glycol (PEG) precipitation as described previously. Details can be found in WO2009098450.

In case further guidance is needed, reference is made to Jespers et al (Protein Engineering Design and Selection 2004 17(10):709-713. Selection of optical biosensors from chemisynthetic antibody libraries.) In one embodiment phage may be purified as taught therein. The text of this publication is specifically incorporated herein by reference for the method of phage purification; in particular reference is made to the materials and methods section starting part way down the right-column at page 709 of Jespers et al.

Moreover, the phage may be purified as published by Marks et al J. Mol. Biol vol 222 pp 581-597, which is specifically incorporated herein by reference for the particular description of how the phage production/purification is carried out.

If phage purification is not desired, culture medium including phage can be mixed directly with a purification resin and a reducing agent (such as TCEP), as set forth in the examples herein.

(iv) Reaction Chemistry

The reaction chemistry can be that set forth in WO2009098450 by Heinis et al., or, preferably, that set forth in EP2970954. Reactions conditions used in the present invention preferably comprise the following steps, all preferably conducted at room temperature:

1. Culture medium from which bacterial cells have been removed, containing phage expressing the desired polypeptide(s), is mixed with buffer, reducing agent and resin equilibrated in buffer.
2. The resin is isolated and resuspended in buffer and dilute reducing agent.
3. The polypeptides are exposed to the molecular scaffold and reacted therewith such that the molecular scaffold forms covalent bonds with the polypeptide.
4. The samples are washed to remove excess unreacted scaffold.
5. Phage are eluted from the resin.

The buffer is preferably pH 8.0; it is not necessary to adjust buffer pH in the final solution. Suitable buffers include $NaHCO_3$, initially at pH 8.0. Alternative buffers may be used, including buffers with a pH in the physiological range, including $NH_4CO_3$, HEPES and Tris-hydroxymethyl aminoethane, Tris, Tris-Acetate or MOPS. The $NaHCO_3$ buffer is preferably used at a concentration of 1M, adding 1 ml to a suspension of resin to equilibrate the resin.

The resin is preferably an ion exchange resin. Ion exchange resins are known in the art, and include any material suitable for anion exchange chromatography known in the art, such as an agarose based chromatography material, e.g. sepharoses like Fast Flow or Capto, polymeric synthetic material, e.g. a polymethacrylate such as Toyopearls, polystyrene/divinylbenzene, such as Poros, Source, or cellulose, e.g. Cellufine. In a preferred embodiment, the anion exchange resin material includes, but is not limited to a resin that carries a primary amine as ligand, e.g. aminohexyl sepharose, benzamidine sepharose, lysine sepharose, or arginine sepharose. In another preferred embodiment, the anion exchange resin material includes, but is not limited to a resin having a positively charged moiety at neutral pH, such as alkylaminoethane, like diethylaminoethane (DEAE), dimethylaminoethane (DMAE), or trimethylaminoethyl (TMAE), polyethyleneimine (PEI), quaternary aminoalkyl, quaternary aminoethane (QAE), quaternary ammonium (Q), and the like.

In step (1), reducing agent is added to a concentration of 1 mM. The dilute reducing agent used in step (2) is preferably at a concentration of 1 µM. Both concentrations are for TCEP, and other values may apply to other reducing agents. The dilute reducing agent is used to maintain the polypeptide in a reduced state prior to reaction with the molecular scaffold. Preferably, a chelating agent is included in the washing step. For example, EDTA may be included.

Alternative reducing agents may be selected from dithiothreitol, thioglycolic acid, thiolactic acid, 3-mercaptopropionic acid, thiomalic acid, 2,3-dimercaptosuccinic acid, cysteine, N-glycyi-L-cysteine, L-cysteinylglycine and also esters and salts thereof, thioglycerol, cysteamine and C1-C4 acyl derivatives thereof, N-mesylcysteamine, Nacetylcysteine, N-mercaptoalkylamides of sugars such as N-(mercapto-2-ethyl) gluconamide, pantetheine, N-(mercaptoalkyl)-cohydroxyalkylamides, for example those described in patent application EP-A-354 835, N-mono- or N,N-dialkylmercapto-4-butyramides, for example those described in patent application EP-A-368 763, aminomercaptoalkyl amides, for example those described in patent application EP-A-432 000, N-(mercaptoalkyl)succinamic acids and N-(mercaptoalkyl)succinimides, for example those described in patent application EP-A-465 342, alkylamine mercaptoalkyl amides, for example those described in patent application EP-A-514 282, the azeotropic mixture of 2-hydroxypropyl thioglycolate and of (2-hydroxy-1-methyl)ethyl thioglycolate as described in patent application FR-A-2 679 448, mercaptoalkylamino amides, for example those described in patent application FR-A-2 692 481, and N-mercaptoalkylalkanediamides, for example those described in patent application EP-A-653 202.

The conjugation of the molecular scaffold, in the case of TBMB and other scaffolds whose reactive groups are thiol-reactive, is preferably conducted in the presence of acetonitrile. The acetonitrile is preferably at a final concentration of about 20%.

Alternative molecular scaffolds to TBMB are discussed herein.

Unreacted molecular scaffold is removed from the phage by washing. Subsequently, phage can be eluted from the resin, and selected as set forth previously.

Additional steps can also be included in the procedure. Such steps are not mandatory, and do not significantly increase the yield or efficiency of the process.

For example, the phage-containing culture medium, combined with the resin, can be washed prior to reduction with the reducing agent. The reducing agent itself can be added in two steps; in a concentrated form, to effect reduction, and then in dilute form (step 2 above), to maintain the displayed polypeptide in a reduced state.

The timing of the steps can also be varied, without significantly altering the efficiency of the procedure. For example, we have found that reduction in TCEP for 20 minutes is as effective as reduction for 30 minutes. Likewise, reaction with TBMB for 10 minutes does not give a significantly lower level of binding than reaction for 30 minutes.

(v) Magnetic Separation

In an advantageous embodiment, the resin is magnetic. This allows the polypeptide-bearing phage to be isolated by magnetic separation. Magnetic resin beads, such as magnetic sepharose beads, can be obtained commercially from, for example, Bangs Laboratories, Invitrogen, Origene and GE Healthcare. See also U.S. Pat. No. 2,642,514 and GB 1239978. Application of a magnetic field permits isolation of the beads, which results in purification of the polypeptides bound to the beads from the medium in which they are contained.

In one embodiment, the magnetic beads are separated from the medium by insertion of a magnetic probe into the medium. Beads are retained on the magnetic probe, and can be transferred to a washing station, or a different medium. Alternatively, beads can be isolated by applying a magnetic field to the vessel in which they are contained, and removing the medium once the beads are immobilised.

Magnetic separation provides faster, more efficient processing of resins in the method of the invention.

(vi) Cell-Based Screening

In accordance with the present invention, modified phage bearing polypeptides encoded as libraries as set forth above are screened against antigens present on cell surfaces, as opposed to in solution as in the prior art.

The general procedure for cell-based screening involves the following steps: firstly, modified phage are prepared as described above in accordance with procedures we have previously described. Both "positive" cells, which express the desired target at the cell surface, and "negative" cells, which do not express the target are required. In a first round of selection, positive cells are blocked with non-specific protein and the library is selected by binding to the positive cells. Cells are incubated with phage under binding conditions, then centrifuged and washed. Bound phage are the eluted and retained.

In the first selection step, no negative selection is used, to ensure the retention of low copy number binder species. In subsequent rounds, however, negative selection is used in which negative cells are incubated with phage under binding conditions, and binding phage are discarded. Cells are blocked with non-specific protein (such as milk) to prevent excessive non-specific binding, and exposed to phage. Phage which bind to the cells under these conditions are considered to have non-specific binding characteristics, and are discarded.

Cycles of positive and negative selection are continued until phage with desired binding properties are isolated. In between each round, phage are multiplied in bacterial hosts to amplify the selected polypeptides, and subsequently modified by scaffold addition before re-selection.

Rounds of selections can be alternated to select ligands which have the capacity to bind homologous targets from different species, or isotypes of the same target within a species. Thus, for example, in selecting a ligand to bind to both murine and human target homologues, rounds of selection can alternate between human and murine targets, selecting positively for human targets and negatively against murine targets in a first round, and reversing the procedure in a second round. In this way, ligands which are selective for one or other target, or non-selective between targets, can be identified.

In another embodiment, two isotypes of a target may be screened in the same manner.

(C) Use of Polypeptide Ligands According to the Invention

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

The peptide ligands of the present invention will typically find use in preventing, suppressing or treating inflammatory states, allergic hypersensitivity, cancer, bacterial or viral infection, and autoimmune disorders (which include, but are not limited to, Type I diabetes, multiple sclerosis, rheumatoid arthritis, systemic lupus erythematosus, Crohn's disease and myasthenia gravis).

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

Methods for the testing of systemic lupus erythematosus (SLE) in susceptible mice are known in the art (Knight et al. (1978) J Exp. Med., 147: 1653; Reinersten et al. (1978) New Eng. J: Med., 299: 515). Myasthenia Gravis (MG) is tested in SJL/J female mice by inducing the disease with soluble AchR protein from another species (Lindstrom et al. (1988) Adv. Inzn7unol., 42: 233). Arthritis is induced in a susceptible strain of mice by injection of Type II collagen (Stuart et al. (1984) Ann. Rev. Immunol., 42: 233). A model by which adjuvant arthritis is induced in susceptible rats by injection of mycobacterial heat shock protein has been described (Van Eden et al. (1988) Nature, 331: 171). Thyroiditis is induced in mice by administration of thyroglobulin as described (Maron et al. (1980) J. Exp. Med., 152: 1115). Insulin dependent diabetes mellitus (IDDM) occurs naturally or can be induced in certain strains of mice such as those described by Kanasawa et al. (1984) Diabetologia, 27: 113. EAE in mouse and rat serves as a model for MS in human. In this model, the demyelinating disease is induced by administration of myelin basic protein (see Paterson (1986) Textbook of Immunopathology, Mischer et al., eds., Grune and Stratton, New York, pp. 179-213; McFarlin et al. (1973) Science, 179: 478: and Satoh et al. (1987) J. Immunol., 138: 179).

Generally, the present peptide ligands will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cylcosporine, methotrexate, adriamycin or cisplatinum, and immunotoxins. Pharmaceutical compositions can include "cocktails" of various cytotoxic or other agents in conjunction with the selected antibodies, receptors or binding proteins thereof of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, including without limitation immunotherapy, the selected antibodies, receptors or binding proteins thereof of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counter-indications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that use levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the selected repertoires of polypeptides described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

(D) Mutation of Polypeptides

The desired diversity is typically generated by varying the selected molecule at one or more positions. The positions to be changed are selected, such that libraries are constructed for each individual position in the loop sequences. Where appropriate, one or more positions may be omitted from the selection procedure, for instance if it becomes apparent that those positions are not available for mutation without loss of activity.

The variation can then be achieved either by randomisation, during which the resident amino acid is replaced by any amino acid or analogue thereof, natural or synthetic, producing a very large number of variants or by replacing the resident amino acid with one or more of a defined subset of amino acids, producing a more limited number of variants.

Various methods have been reported for introducing such diversity. Methods for mutating selected positions are also well known in the art and include the use of mismatched oligonucleotides or degenerate oligonucleotides, with or without the use of PCR. For example, several synthetic antibody libraries have been created by targeting mutations to the antigen binding loops. The same techniques could be used in the context of the present invention. For example, the H3 region of a human tetanus toxoid-binding Fab has been randomised to create a range of new binding specificities (Barbas et al. (1992) Proc. Natl. Acad. Sci. USA, 89: 4457). Random or semi-random H3 and L3 regions have been appended to germline V gene segments to produce large libraries with mutated framework regions (Hoogenboom- & Winter (1992) R Mol. Biol., 227: 381; Barbas et al. (1992) Proc. Natl. Acad. Sci. USA, 89: 4457; Nissim et al. (1994) EMBO J, 13: 692; Griffiths et al. (1994) EMBO J, 13: 3245; De Kruif et al. (1995) J. Mol. Biol., 248: 97). Such diversification has been extended to include some or all of the other antigen binding loops (Crameri et al. (1996) Nature Med., 2: 100; Riechmann et al. (1995) BiolTechnology, 13: 475; Morphosys, WO97/08320, supra).

However, since the polypeptides used in the present invention are much smaller than antibodies, the preferred method is to synthesise mutant polypeptides de novo. Mutagenesis of structured polypeptides is described above, in connection with library construction.

The invention is further described below with reference to the following examples.

EXAMPLES

Unless otherwise stated, any methods and materials similar or equivalent to those described herein can be used in the practice or testing of the present invention. Methods, devices, and materials suitable for such uses are described above. All publications cited herein are incorporated herein by reference in their entirety for the purpose of describing and disclosing the methodologies, reagents, and tools reported in the publications that might be used in connection with the invention.

Example 1: Protocol for Cell-Based Selection

Material and Methods
Scaffold-modified library aliquots

Figure 9:
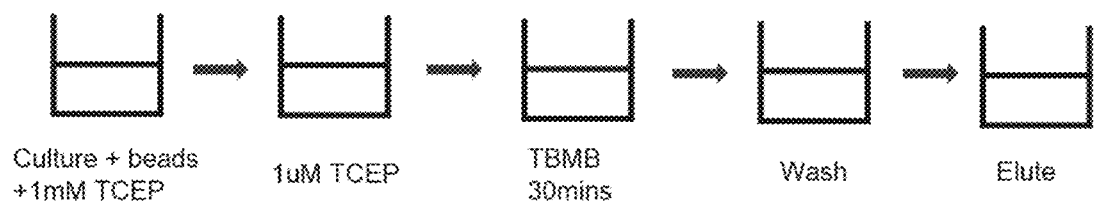
FIG. 9 illustrates the steps of the Kingfisher modification.

Cell expressing target (Positive cells)
Cell non expressing target (negative cells)
PBS (Sigma D8537)
20% FBS (Foetal Bovine Serum, Sigma #F7524) in PBS
Skim Milk Powder (Sigma #70166)
1M NaHCO$_3$
'SuporQ' ion exchange beads (Biotoolomics 'Magnetic SepFast SuporQ'; stored at RT)
Degassed carbonate (modification) buffer (20 mM NaHCO$_3$+5 mM EDTA in ultrapure H2O)
1M TCEP (Thermo Scientific #20491 (or equiv.: CAS 51805-45-9); made up to 1M in ultrapure H2O and stored at −20° C.)
5× Scaffold in acetonitrile (stored at −20° C.)
TBMB (Sigma #657336; stock at 1M in acetonitrile at −20° C.)
Acetonitrile (VWR #20060.320 (or equiv.: CAS 75-05-8))
50 mM citrate 1.5M NaCl pH5
Citric acid (Sigma #C0759 (or equiv.: CAS 77-92-9))
5M NaCl (Sigma #S6316)
1M Tris pH8 (Sigma #T2694)
50% glycerol (Sigma #G5516 (or equiv.: CAS 56-81-5); dilute to 10% in HyClone ultrapure H2O)
50 mM Glycine-HCl pH2.2 (Sigma #50046 (or equiv.: CAS 56-40-6))
TG1 *E. coli.* (prepared in-house; aliquots at −80° C.)
2YT (Melford #M2104; autoclaved)
Tetracycline stock solution (Melford #T0150 (or equiv.: CAS 64-75-5); stock at 12.5 mgml-1 in 70% EtOH at −20° C.; see 'Media & Reagents Protocols' Excel file)
50 ml vented tubes (TPP 'Filter Tubes 50 Bioreactor' #87050)
Tetracycline LB-agar plates (incl. 15 cm where required). [Tet]=12.5 ugml-1
LB-agar (Melford #L2418; autoclaved)
Tetracycline stock solution
Kingfisher liquid handling system and associated strips & rod covers Phage Preparation
1. Prepare (Modify) Input Phage
Round 1
For Round 1, stock aliquots of libraries are used. These are typically stored in TBMB-modified form, and stored as appropriately-sized aliquots. The aim is to include at least 10× more infectious phage than the size of the library. The selection is performed in 1000 µl, so this puts a limit on how many phages can be used. Each aliquot typically will contain $10^{12}$-$10^{13}$ phage.
  Use one aliquot of stored TBMB-modified library per selection (typically 100 ul)
Subsequent Rounds
For Round 2 and onwards, the output phage from the previous round are amplified via infection and overnight growth of TG1, and then TBMB-modified using the Kingfisher liquid handling system. This enables more selection samples to be modified in parallel (often a selection will diverge to incorporate different concentrations of target in the later rounds).
  Remove 1 ml of the infected overnight TG1 output cultures and generate glycerol stock (1 ml culture+500 ul 50% glycerol). Store at −80° C.
  Degas the 20 mM NaHCO3/5 mM EDTA buffer (modification buffer), by pulse sonicating under vacuum for 10 mins
  Prepare 1 ml of 1 mM TCEP in modification buffer
  Determine the number of selection samples required: E.g. if 3 concentrations of target are to be used, then 3×1 ml of the culture must be processed; if this is also to be performed with selections from 3 libraries, then the total number of selection samples will be 3×3=9 (in such cases, it is recommended that enough reagents for n+1 are prepared).
  For each selection sample, prepare 1 ml 1 µM TCEP/modification buffer (using the 1 mM TCEP from above)
  For each selection sample, prepare 1 ml 20% acetonitrile/60 µM TBMB/modification buffer (e.g. For 10 samples: 8 ml modification buffer+2 ml 300 µM TBMB in ACN)
  For each selection sample, wash 20 ul SuporQ ion exchange bead slurry 3× in 1 ml 1M NaHCO$_3$. For multiple samples, the beads can be washed together.
  Resuspend the beads in 20 ul 1M NaHCO$_3$ (per 20 ul bead slurry). Therefore, for every 20 ul bead slurry, the final bead+buffer volume will be ~33 ul.
  To the washed beads, add 1 M TCEP: 1 ul per sample (such that when made up to 1 ml, [TCEP]final=1 mM; NB. Bubbles should be formed)
  Add the ~33 ul washed beads/TCEP to well A of the Kingfisher, and add 970 ul of the overnight infected TG1 culture
  Load Kingfisher wells as follows:
  1 ml input solution (Culture/beads/TCEP)
  1 ml modification buffer+1 µM TCEP
  1 ml modification buffer/60 µM TBMB/20% ACN
  1 ml modification buffer
  50 ul 50 mM citrate/1.5M NaCl/pH5 elution buffer
  Run the '10 min TBMB' Kingfisher programme follows:
  Mix 20 mins
  Mix 5 sec
  Mix 10 min
  Mix 1 min
  Mix 1 min; release beads into well D
  Overall, the Kingfisher modification performs the steps outlined in FIG. 9.
  20 mins
Wash Beads in 1M NaHCO$_3$, Add TCEP, then Add Culture
10 mins
50 mM Citrate, 1.5MNaCl, pH5
  Transfer the eluates to eppendorf tubes and add 10 ul 1 M Tris pH8 to neutralise them
  Retain 1-2 ul for titre (if desired).
Selection Protocol
  Defrost one vial of the positive cells (1×107 cells/ml) dilute the cells at least 1/10 in PBS in a 14 ml falcon tube.
  Centrifuge the cells for 5 min at 1000 rpm at 4° C.
  Discard the supernatant, and wash once the cells by resuspending the pellet in 1 ml of 20% FBS.
  Centrifuge the cells for 5 min at 1000 rpm at 4° C.
  Resuspend the pellet in 1 ml of PMF (20% FBS+4% Milk+30 mM HEPES in PBS pH 7.4) and incubate at 4° C. for 1 h on a rotating wheel
  Centrifuge the cells for 5 min at 1000 rpm at 4° C.
  Discard the supernatant and add the deselected phage and incubate at 4° C. for 1 h on a rotating wheel
  Wash with 20% FBS by centrifugation 5 min at 1000 rpm at 4° C. o R1 3 Washes with 3 ml 20% and 1 PBS wash with 1 ml removed by pipetting o R2 5 washes 3 ml 20% FBS and 1 PBS wash with 1 ml removed by pipetting
  R3 & R4 8 washes 3 ml 20% FBS+1 Washes with 3 ml PBS and 1 PBS wash with 1 ml removed by pipetting After the last wash, resuspend the cells in a 1.5 ml Eppendorf tube with 300 ul of 50 mM Glycine-HCl pH 2.2, and incubate 10-15 min at 4° C. on a rotating wheel.

Centrifuge the cells at 14000 rpm for 5 min, discard the pellet and neutralise the supernatant with 60 ul of 1 M Tris pH8.

Deselection Protocol

The deselection step using negative cells will allow removing most of the non-specific binders. The deselection in this case is performed on HEK-293F cells which are not expressing the target.

Defrost one vial of the negative cells ($1 \times 10^7$ cells/ml), dilute the cells at least 1/10 in PBS in a 14 ml falcon tube.

Centrifuge the cells for 5 min at 1000 rpm at 4° C.

Discard the supernatant, and wash once the cells by resuspending the pellet in 1 ml of 20% FBS.

Centrifuge the cells for 5 min at 1000 rpm at 4° C.

Resuspend the pellet in 1 ml of PMF (20% FBS+4% Milk+30 mM HEPES in PBS pH 7.4) and incubate at 4° C. for 1 h on rotating wheel.

After the 1 h incubation, add the 60 ul phage elution into the cells and incubate at 4° C. for 1 h on rotating wheel to allow the deselection.

Centrifuge the cells for 5 min at 1000 rpm at 4° C. and keep the supernatant.

Infection, Titre & Growth

Inoculate 25 ml 2YT with a 50 µl frozen aliquot of TG1 *E. coli* in a 250 ml vented flask Incubate at 37° C. with shaking at 250 rpm until Abs(600 nm)=0.6 (~2 hrs)

In 50 ml TPP vented tubes, add the selection outputs (~360 µl) to 1 ml culture

Incubate at 37° C. shaking 250 rpm for 1 hr

Retain 4 µl for titre (see below)

Add 5 ml 2YT/tetracycline ([tet]=12.5 ugml$^{-1}$) to each 1 ml output culture

Incubate overnight at 370 C shaking 250 rpm

Take 1 ml of the overnight output culture and store as a glycerol stock at −800 C (add 500 µl 50% glycerol to 1 ml)

Or:

Spread each 1 ml output culture on a dry 15 cm tet/LB-agar plate

Incubate overnight at 37° C., or for ~3 days at RT

Add ~2 ml 2:1 2YT:50% glycerol to each plate and thoroughly scrape off the bacteria Pipette gently to resuspend the bacteria and transfer to cryovials for storage at −80° C.

For a subsequent round of selection, inoculate 25 ml 2YT/tetracycline with 100 µl of the scraped material and incubate overnight at 37° C. shaking 250 rpm.

Phage Titre

Titre for R1 & R2:

Dilute 4 µl of infected culture (see above) in 96 µl 2YT (1 in 25 dilution)

Generate $8 \times 10$-fold serial dilutions (from 1 in 25 to 1 in 2.5e8) in 2YT Spot 20 µl of each dilution onto dried tet/LB-agar plates Incubate overnight at 37° C., or ~3 days at RT Count the colonies and calculate the infective titre of the selection outputs.

Titre for R3 Onwards (Plate Out for Screening):

plate out the 80 uL left of each of the three most concentrated dilutions onto individual plates Incubate overnight at 37° C., or ~3 days at RT Example 2

Selection of a Library Using Cell-Based Screening

Libraries were created using the scaffolds TBMB and TATA according to the methodology described above. CCR4 is a GPCR expressed on immune cells; previously, we have not been successful in isolating a peptide ligand specific for CCR4. Here, we select libraries against GPCR and determine that the cell-based selection platform can be applicable to transmembrane protein like GPCRs.

Aim

To carry out at least 4 rounds of selections against CCR4 HEK transfected cells with the TATA and TBMB libraries pooled libraries and identify any CCR4-binding clones.

Materials and Methods

As specified in Example 1. 2 Mixes of libraries were made for each scaffold using one aliquot for each: Symmetric libraries (3×3, 4×4, 5×5, 6×6); and Structured libraries (2×6, 2×7, 7×2, 7×3, 3×7, 3×6, 6×3, 3×9). TATA is used at a concentration of 400 µM for peptide modification.

Results:

All the mix libraries (TATA and TBMB) showed an enrichment at round 3 with a good Signal to Background at round 4 of the selection procedure The structured libraries performed better compared to the symmetric libraries which might be a good indication that the selections are working well. Indeed, most of antibodies targeting GPCRs have a long CDR (Complementarity-determining region) to get into the pocket. So, having a small loop and a big loop for bicyclic peptide ligand may be appropriate.

A lot of 4 cysteines clones have been enriched during the selection.

Figure 10:
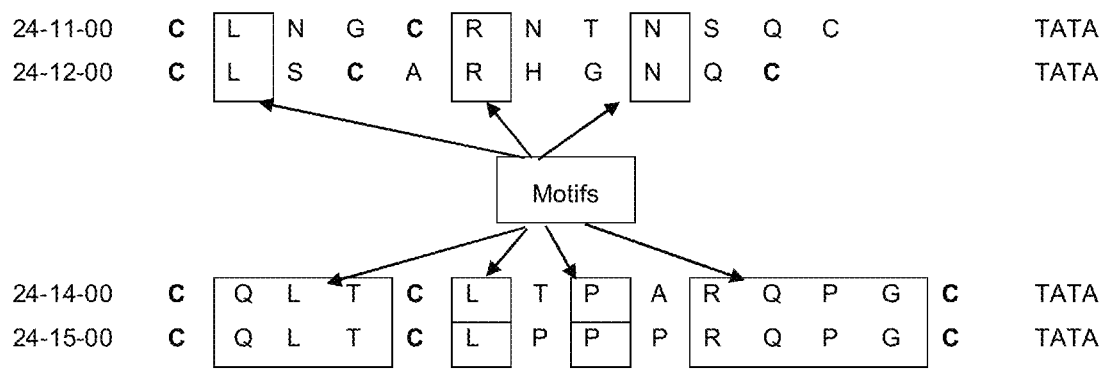
FIG. 10 illustrates motifs identified in cell-based screening.

Motifs were identified, as shown in FIG. 10.

24 bicyclic peptide ligand clones have been screened against HEK-CCR4 cells on a cell based ELISA using the following protocol:

$1 \times 10^7$ HEK parent and $1 \times 10^7$ HEK-CCR4 cells were thawed quickly in warm water.

Cells were resuspended and washed two times in 10 ml PBS and centrifuged for 5 min at 1000 RPM Cells were resuspended in 10 ml of PMF giving $1 \times 10^6$ cells/ml and 100 ul of cells were seeded into a 96 well plate for 1 h on ice (half a plate of HEK-CCR4 cells and the other half with HEK parental cells)

5 ul of neutralized phage is added to the cells after modification and incubated 1 h on ice Cells are washed three times with 200 ul of PBS by centrifugation for 5 min at 1000 RPM 100 ul Anti-M13 HRP (GE #27942101) in PMF (diluted 1:5000) is added to the cells for 1 h on ice Cells are washed three times with 200 ul of PBS by centrifugation for 5 min at 1000 RPM 100 ul of TMB (ThermoFisher #N301) is added to the cells for 10 min and the reaction is stopped with 1% HCl Plate is read onto Pherastar using Absorbance programme at 450.

Positive binding clones were obtained, as shown in FIG. X.

The following peptides were synthesized for further analysis:

| | | | | | | | | | | | | | | |
|---|---|---|---|---|---|---|---|---|---|---|---|---|---|---|
| 24-11-00 | C | L | N | G | C | R | N | T | N | S | Q | C | | TATA | P-024-003 | A01 |
| 24-12-00 | C | L | S | C | A | R | H | G | N | Q | C | | | TATA | P-024-003 | B01 |
| 24-13-00 | C | P | L | M | S | S | V | N | C | T | A | G | C | TBMB | P-024-003 | G03 |
| 24-14-00 | C | Q | L | T | C | L | T | P | A | R | Q | P | G | C | TATA | P-024-003 | E01 |
| 24-15-00 | C | Q | L | T | C | L | P | P | P | R | Q | P | G | C | TATA | P-024-003 | C01 |
| 24-16-00 | C | Q | T | L | C | N | T | A | E | D | I | R | C | | TBMB | P-024-003 | H03 |
| 24-17-00 | C | R | A | V | H | S | L | R | C | L | T | T | C | | TATA | P-024-003 | F01 |

Example 3

Analysis of CCR4 Peptide Ligands Obtained by Cell-Based Screening

Several naked peptides were found by naïve pilot screening as described in Example 2, and were synthesized.

The aim of the present experiment was to analyze if if these peptides are functional using a Discoverx Assay, the Beta-Arrestin recruitment assay, to identify agonism or antagonism in the selected peptides.

Experimental & Results

Standard protocols used:
PathHunter® eXpress CCR4 CHO-K1 β-Arrestin GPCR Assay. 100 dp (1×96-well)
93-0193e2cp0s
CCL22 Discoverx (Cat no #92-1006)
Peptides in 100% DMSO

| | | |
|---|---|---|
| 24-11-00-N001 | | ACLNGCRNTNSQCA |
| 24-12-00-N001 | | ACLSCARHGNQCA |
| 24-13-00-N001 | | ACPLMSSVNCTAGCA |
| 24-14-00-N001 | | ACQLTCLTPARQPGCA |
| 24-15-00-N001 | | ACQLTCLPPPRQPGCA |
| 24-16-00-N001 | | ACQTLCNTAEDIRCA |
| 24-17-00-N001 | | ACRAVHSLRCLTTCA |

The experiment was carried using the manufacturer instructions.

| | | 375 nM Raw Data 1 | 125 nM 2 | 41.7 nM 3 | 13.9 nM 4 | 4.6 nM 5 | 1.5 nM 6 | 0.51 nM 7 | 0.17 nM 8 | 0.06 nM 9 | 0.02 nM 10 | 0.006 nM 11 | 0 12 |
|---|---|---|---|---|---|---|---|---|---|---|---|---|---|
| 24-11-00-N001 | A | 19528 | 22195 | 22581 | 22941 | 26096 | 27602 | 27976 | 25757 | 27885 | 24123 | 24609 | 26291 |
| 24-12-00-N001 | B | 22486 | 25288 | 26640 | 27830 | 28872 | 31584 | 34202 | 27668 | 30311 | 30201 | 31416 | 26137 |
| 24-13-00-N001 | C | 20081 | 22524 | 23071 | 24436 | 29431 | 34513 | 31217 | 31512 | 30335 | 30705 | 27634 | 27675 |
| 24-14-00-N001 | D | 20214 | 21899 | 24892 | 24521 | 27510 | 30785 | 32968 | 28531 | 30232 | 25603 | 28548 | 28296 |
| 24-15-00-N001 | E | 24222 | 22916 | 24463 | 25509 | 27635 | 30670 | 31189 | 28025 | 26888 | 27298 | 28566 | 28341 |
| 24-16-00-N001 | F | 20361 | 20012 | 20583 | 20756 | 22899 | 24736 | 25030 | 25062 | 25748 | 23757 | 23153 | 27877 |
| 24-17-00-N001 | G | 22611 | 23999 | 23928 | 23972 | 25017 | 27917 | 27025 | 29746 | 29865 | 26107 | 27836 | 28331 |
| CCL22 | H | 234176 | 249665 | 230085 | 209362 | 172692 | 135687 | 111988 | 84488 | 57093 | 41715 | 37757 | 27559 |

No agonism was detected in the assayed peptides at the concentrations set forth in the above table except with CCL22, the natural ligand, which possessed an activity as expected with an EC50=1.646e-009.

The concentration was increased to test for response at high concentration.

| | | 50 uM Raw Data 1 | 16.7 uM 2 | 5.6 uM 3 | 1.9 uM 4 | 0.6 uM 5 | 0.2 uM 6 | 0.1 uM 7 | 0.023 uM 8 | 0.008 uM 9 | 0.003 uM 10 | 0.001 uM 11 | 0 uM 12 |
|---|---|---|---|---|---|---|---|---|---|---|---|---|---|
| 24-11-00-N001 | A | 9993 | 10968 | 10444 | 11006 | 11009 | 12202 | 11394 | 11338 | 10183 | 10549 | 9494 | 9576 |
| 24-12-00-N001 | B | 12457 | 12407 | 12922 | 13661 | 13041 | 13783 | 13063 | 12540 | 11106 | 11299 | 10679 | 11402 |
| 24-13-00-N001 | C | 11512 | 12506 | 12460 | 12391 | 12989 | 13560 | 13168 | 12684 | 12612 | 11640 | 11252 | 11916 |
| 24-14-00-N001 | D | 13314 | 12239 | 12720 | 12725 | 12839 | 13151 | 12143 | 12607 | 12385 | 11788 | 10817 | 11683 |
| 24-15-00-N001 | E | 10917 | 13469 | 13067 | 13457 | 13586 | 13225 | 13265 | 12121 | 12079 | 11501 | 10900 | 9174 |
| 24-16-00-N001 | F | 13817 | 13237 | 14263 | 14247 | 14951 | 13403 | 13482 | 12701 | 12502 | 11906 | 10927 | 9225 |
| 24-17-00-N001 | G | 16749 | 16709 | 17261 | 17244 | 15965 | 15518 | 14856 | 13984 | 13248 | 11809 | 11608 | 10798 |
| CCL22 | H | 122799 | 130064 | 118686 | 118822 | 101987 | 88410 | 67642 | 47935 | 29739 | 23261 | 16366 | 11611 |

Again, no agonism was detected except for the natural ligand CCL22.

We therefore used the assay in an antagonist format, using 10 nM CCL22.

|  |  | 50 uM Raw Data 1 | 16.7 uM 2 | 5.6 uM 3 | 1.9 uM 4 | 0.6 uM 5 | 0.2 uM 6 | 0.1 uM 7 | 0.023 uM 8 | 0.008 uM 9 | 0.003 uM 10 | 0.001 uM 11 | 0 uM 12 |
|---|---|---|---|---|---|---|---|---|---|---|---|---|---|
| 24-11-00-N001 | A | 119853 | 127180 | 145586 | 153353 | 163219 | 151383 | 154951 | 154833 | 146640 | 157449 | 164482 | 18984 |
| 24-12-00-N001 | B | 134429 | 163675 | 164381 | 197426 | 207362 | 197817 | 168443 | 176223 | 193071 | 192263 | 162386 | 22059 |
| 24-13-00-N001 | C | 133745 | 179127 | 180947 | 194535 | 181254 | 195355 | 170995 | 183445 | 201223 | 200825 | 195228 | 23052 |
| 24-14-00-N001 | D | 138731 | 132736 | 150686 | 143688 | 158845 | 151985 | 168602 | 159753 | 156373 | 138339 | 163937 | 20184 |
| 24-15-00-N001 | E | 55746 | 94688 | 119202 | 149995 | 164042 | 160790 | 162443 | 163145 | 159966 | 152456 | 166495 | 19944 |
| 24-16-00-N001 | F | 138655 | 167890 | 140714 | 143871 | 147765 | 159872 | 157585 | 158472 | 142089 | 169611 | 155442 | 20336 |
| 24-17-00-N001 | G | 153988 | 140316 | 148721 | 132070 | 146982 | 151630 | 153182 | 164921 | 143078 | 174559 | 164018 | 19479 |
| CCL22 | H | 223579 | 245795 | 212050 | 175875 | 173881 | 169306 | 151947 | 131693 | 136281 | 150444 | 178148 | 18030 |

In this case, we saw that some of the peptides are showing an antagonism activity. 24-11 and 24-15 showed the best curve with an IC80 respectively of 9.288 uM and 14 uM. The other IC50 values could not be accurately determined.

We repeated this experiment lowering the concentration of CCL22 from 10 nM to 1 nM to show a full inhibition curve.

Materials:
Human MMP-14 PEX protein at 71.1 μM monomer (previously 77.1 μM) (T-017-011), stored in fridge (4/7/14)

Peptides as described in Results section

Method:
Prepare assay buffer: 20 mM HEPES, 150 mM NaCl, 1 mM CaCl2), 0.1% Tween20 (pH 7.6). Buffer was filtered before use to remove precipitate.
Method according to Example 3 with tracer at 1 nM and MMP-14 PEX at concentrations detailed in the graphs

|  |  | 50 uM Raw Data 1 | 16.7 uM 2 | 5.6 uM 3 | 1.9 uM 4 | 0.6 uM 5 | 0.2 uM 6 | 0.1 uM 7 | 0.023 uM 8 | 0.008 uM 9 | 0.003 uM 10 | 0.001 uM 11 | 0 uM 12 |
|---|---|---|---|---|---|---|---|---|---|---|---|---|---|
| 24-11-00-N001 | A | 85131 | 106271 | 110179 | 129872 | 141369 | 136037 | 132431 | 155622 | 158208 | 146107 | 139740 | 27599 |
| 24-12-00-N001 | B | 101311 | 123432 | 225342 | 184486 | 195159 | 196279 | 190863 | 200429 | 216507 | 230925 | 205771 | 29480 |
| 24-13-00-N001 | C | 114497 | 156536 | 200574 | 190843 | 229977 | 228712 | 218869 | 219415 | 210841 | 230497 | 229814 | 30412 |
| 24-14-00-N001 | D | 102610 | 116828 | 171795 | 198268 | 200525 | 201484 | 215827 | 212035 | 212749 | 222439 | 240299 | 30778 |
| 24-15-00-N001 | E | 37690 | 47343 | 168855 | 210573 | 230668 | 233858 | 267763 | 265078 | 278839 | 269008 | 244512 | 34410 |
| 24-16-00-N001 | F | 107480 | 150731 | 186217 | 213016 | 213774 | 225038 | 246609 | 247868 | 249215 | 250550 | 244145 | 32847 |
| 24-17-00-N001 | G | 114156 | 125610 | 197381 | 240952 | 252179 | 246983 | 296795 | 285103 | 301675 | 292052 | 272073 | 36533 |
| CCL22 | H | 508067 | 433500 | 422771 | 425613 | 321207 | 245828 | 225758 | 218834 | 204398 | 206356 | 189754 | 32745 |

This experiment allowed us to confirm that 24-15 is an antagonist for CCR4 as is 24-14, which is related to the 24-15 clone. We have therefore successfully isolated clones from phage display cell-based selection against a GPCR showing an activity. 24-15 clone shows an antagonism activity in the micromolar range.

The next step is to carry on affinity maturation on 24-15 to improve the affinity and get a better IC50.

60 min data analysed
Results are shown in FIG. 6.
Through cell-based screening, we have identified two other families:
17-98 family which binds to the same site as the 17-88 family (the collagen binding site);
17-99 family which binds to a novel binding site. The 17-99 family competes with all the other families.

| 17-98 | C | K | M | E | S | W | E | C | L | M | L | H | P | K | C |
| 17-99 | C | Q | N | R | F | P | N | C | P | I | N | G | F | F | C |
| 17-88 | C | P | Y | S | W | E | T | C | L | F | G | D | Y | R | C |
| 17-69-07 | C | Y | N | E | F | G | C | E | D | F | Y | D | I | C |

Example 4

Analysis of MT-MMP Peptides 17-69-07 and 17-88 peptide ligands were previously isolated from soluble selections against the MT1-MMP hemopexin domain.

The 17-88 family of peptide ligands binds to the collagen binding site and the 17-69-07 family binds to a neutral binding site. Therefore, they do not cross compete.

We sought to discover new MT1-MMP binding ligands through cell-based screening.

Figure 7:
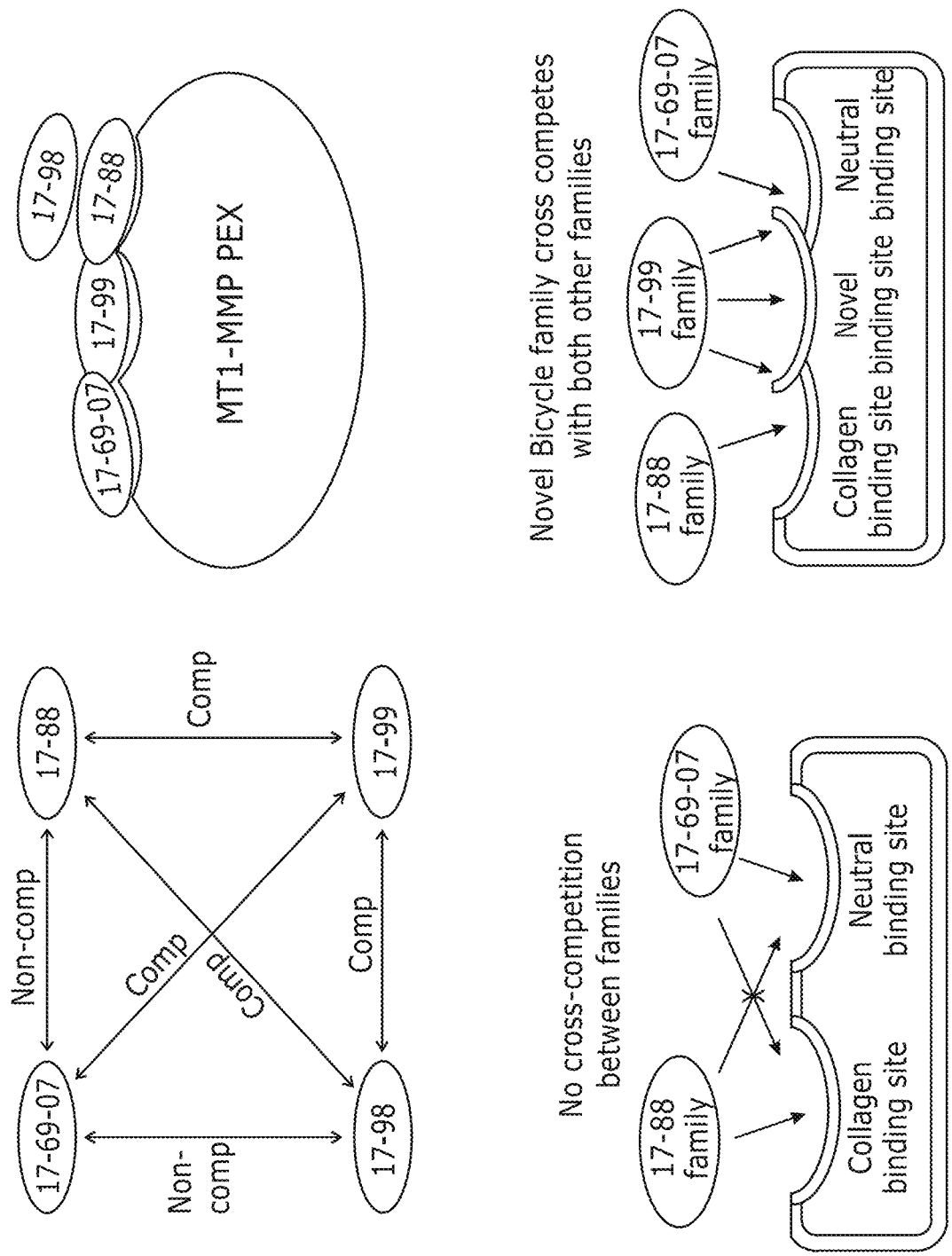
FIG. 7 illustrates the competition profile between peptide ligands isolated in this example.
Figure 8:
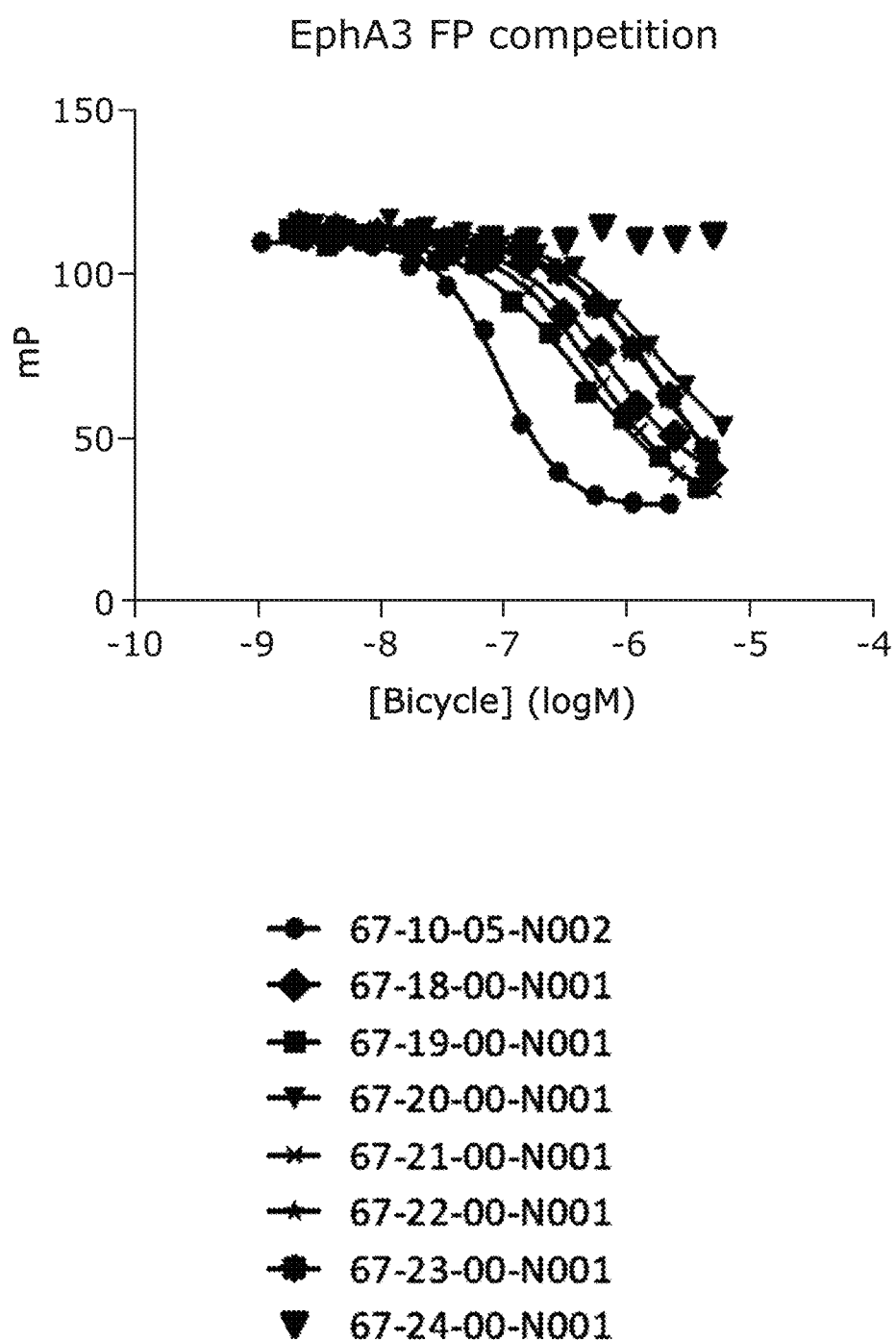
FIG. 8 illustrates an FP competition assay in which EphA3 peptide ligand 67-10-05 was used as a labelled tracer. Six peptides were identified (67-18-00, 67-19-00, 67-20-00, 67-21-00, 67-22-00, 67-23-00 and 67-24-00).

The data suggest that 17-99 binds in a pocket that overlaps the binding site for all the other peptides, whereas the 17-69-07 binding site is distinct from the 17-88/17-98 binding site (this of course ignores any allosteric communication). See FIG. 7.

Example 5

Analysis of EphA3 Peptides

Phage display has previously identified a number of naïve peptide binders, two of which have been taken forward into affinity maturation. So far all selections have been performed with soluble EphA3 ecto domain.

Further naive selections were performed using a cell based target and using 2×7 and 6×6 pasylated (PAS) libraries. A naïve binding peptide was identified in selections using the 2×7 TATA library, the result of a fortuitous mutation. Subsequently a new naïve 2×6 library was constructed. This library was then used in this set of selections.

Cell based selections were performed using the standard protocol (see above examples) with the exception of round 3. Round 2 outputs were processed in 2 ways. One set of outputs were put into standard cell based selections, whilst a second set of outputs were processed using a soluble selection protocol using 10 nM target concentration. A plate of round 3 outputs were sequenced and screened for each selection from both the soluble and cell based selection formats.

Output numbers were high at pound 1 and very low at round 2. Significant enrichment was seen at R3 in both the cell based and soluble selections. The only exception was the 2×6 library which showed no enrichment at round 3 in the soluble selections and markedly less than in the 2×7PAS and 6×6PAS cell based selections.

After four rounds of naïve selections using the cell-based screening process, six peptides were identified (67-18-00, 67-19-00, 67-20-00, 67-21-00, 67-22-00, 67-23-00 and 67-24-00).

All peptides identified through cell-based screening competed with the family identified via soluble selection except 67-24-00 which appeared to be a non-binder.

| Peptide | Loop size | Ki (nM) | Sequences |
|---|---|---|---|
| 67-10-05-N005 | 6X6 | 5.39 | CIPDPYQCVILRQPC |
| 67-18-00-N001 | 2X7 | 104 | CAVCPYPAGVSC |
| 67-19-00-N001 | 2X7 | 47 | CYHCFFPDHNPC |
| 67-20-00-N001 | 2X7 | 238 | CAYCFYPEMNPC |
| 67-21-00-N001 | 6X6 | 77.9 | CDTRFWWCRGPTRLC |
| 67-22-00-N001 | 6X6 | 231 | CGKPIWSCPMTPNLC |
| 67-23-00-N001 | 6X6 | 263 | CGYSLLTCTWKEWDC |
| 67-24-00-N001 | 6X6 | No binding | CRASAGQCNPDPKLC |

The invention claimed is:

1. A method for screening a library of peptide ligands that bind to a cell surface, said library comprising a plurality of polypeptides covalently linked to a molecular scaffold at three or more amino acid residues, comprising the steps of:
   (a) displaying said library of peptide ligands in a genetic display system, wherein the polypeptide comprises three or more reactive groups, each of which forms a covalent linkage to the molecular scaffold, and at least two loops, each of which comprises a sequence of amino acids subtended between two of said reactive groups;
   (b) exposing the peptide ligands to one or more target molecules which are present in a lipid bilayer membrane system during the screening; and
   (c) screening the peptide ligands for binding against the target, and selecting the ligands which bind to the target,
   wherein the peptide ligands bind in a pocket on the target on the surface or close to the surface.

2. The method according to claim 1, wherein the genetic display system is phage display.

3. The method according to claim 1, wherein the library of peptide ligands has a complexity of at least $10^4$, $10^5$, $10^6$, $10^7$, $10^8$, $10^9$, $10^{10}$ or more peptide ligands.

4. The method according to claim 1, wherein the lipid bilayer membrane system displaying the target molecule is selected from a mammalian cell, an insect cell, a bacterial cell, a yeast cell, a membrane preparation from a cell, an artificial membrane, a liposome and a virus-like particle.

5. The method according to claim 1, wherein the library is further deselected by screened against cells not displaying the target molecule to remove non-specific peptide ligands.

6. The method according to claim 1, including multiple rounds of selection against the target molecule and deselection against cells lacking the target molecule.

7. The method according to claim 6, where the polypeptides are amplified between rounds of selection.

8. The method according to claim 1, wherein the target molecule is a cell surface molecule.

9. The method according to claim 8, wherein the target molecule is selected from EphA3, β1 Adrenergic receptor, CCR4, CD38, Claudin 18.2 and MT1-MMP.

10. The method according to claim 8, wherein the peptide ligands cannot be selected against the target molecule in solution.

11. The method according to claim 1, wherein the library of peptide ligands is further screened for resistance to a specific tissue environment.

12. The method according to claim 11, wherein the library of ligands is screened for resistance to proteases, extracellular enzymes or to low pH.

13. The method according to claim 1, wherein the library of peptide ligands is screened for cross-reactivity between targets from two different species or of two different isotypes.

14. The method according to claim 1, wherein each peptide ligand in the library of peptide ligands comprises three or more reactive groups covalently linked to a molecular scaffold.

15. The method according to claim 1, wherein the peptide ligands are multispecific.

16. The method according to claim 9, wherein the peptide ligands cannot be selected against the target molecule in solution.

17. The method of claim 1, wherein the reactive groups of the polypeptide comprise cysteine residues.

* * * * *

SEQUENCE LISTING

<160> NUMBER OF SEQ ID NOS: 26

<210> SEQ ID NO 1
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Cys Leu Asn Gly Cys Arg Asn Thr Asn Ser Gln Cys
1               5                   10

<210> SEQ ID NO 2
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Cys Leu Ser Cys Ala Arg His Gly Asn Gln Cys
1               5                   10

<210> SEQ ID NO 3
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Cys Gln Leu Thr Cys Leu Thr Pro Ala Arg Gln Pro Gly Cys
1               5                   10

```
<210> SEQ ID NO 4
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Cys Gln Leu Thr Cys Leu Pro Pro Pro Arg Gln Pro Gly Cys
1               5                   10

<210> SEQ ID NO 5
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Cys Pro Leu Met Ser Ser Val Asn Cys Thr Ala Gly Cys
1               5                   10

<210> SEQ ID NO 6
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Cys Gln Thr Leu Cys Asn Thr Ala Glu Asp Ile Arg Cys
1               5                   10

<210> SEQ ID NO 7
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Cys Arg Ala Val His Ser Leu Arg Cys Leu Thr Thr Cys
1               5                   10

<210> SEQ ID NO 8
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ala Cys Leu Asn Gly Cys Arg Asn Thr Asn Ser Gln Cys Ala
1               5                   10

<210> SEQ ID NO 9
<211> LENGTH: 13
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ala Cys Leu Ser Cys Ala Arg His Gly Asn Gln Cys Ala
1               5                   10

<210> SEQ ID NO 10
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Ala Cys Pro Leu Met Ser Ser Val Asn Cys Thr Ala Gly Cys Ala
1               5                   10                  15

<210> SEQ ID NO 11
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ala Cys Gln Leu Thr Cys Leu Thr Pro Ala Arg Gln Pro Gly Cys Ala
1               5                   10                  15

<210> SEQ ID NO 12
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ala Cys Gln Leu Thr Cys Leu Pro Pro Pro Arg Gln Pro Gly Cys Ala
1               5                   10                  15

<210> SEQ ID NO 13
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ala Cys Gln Thr Leu Cys Asn Thr Ala Glu Asp Ile Arg Cys Ala
1               5                   10                  15

<210> SEQ ID NO 14
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 14

Ala Cys Arg Ala Val His Ser Leu Arg Cys Leu Thr Thr Cys Ala
1               5                   10                  15

<210> SEQ ID NO 15
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Cys Lys Met Glu Ser Trp Glu Cys Leu Met Leu His Pro Lys Cys
1               5                   10                  15

<210> SEQ ID NO 16
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Cys Gln Asn Arg Phe Pro Asn Cys Pro Ile Asn Gly Phe Phe Cys
1               5                   10                  15

<210> SEQ ID NO 17
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Cys Pro Tyr Ser Trp Glu Thr Cys Leu Phe Gly Asp Tyr Arg Cys
1               5                   10                  15

<210> SEQ ID NO 18
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Cys Tyr Asn Glu Phe Gly Cys Glu Asp Phe Tyr Asp Ile Cys
1               5                   10

<210> SEQ ID NO 19
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

```
Cys Ile Pro Asp Pro Tyr Gln Cys Val Ile Leu Arg Gln Pro Cys
1               5                   10                  15
```

<210> SEQ ID NO 20
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

```
Cys Ala Val Cys Pro Tyr Pro Ala Gly Val Ser Cys
1               5                   10
```

<210> SEQ ID NO 21
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

```
Cys Tyr His Cys Phe Phe Pro Asp His Asn Pro Cys
1               5                   10
```

<210> SEQ ID NO 22
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

```
Cys Ala Tyr Cys Phe Tyr Pro Glu Met Asn Pro Cys
1               5                   10
```

<210> SEQ ID NO 23
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

```
Cys Asp Thr Arg Phe Trp Trp Cys Arg Gly Pro Thr Arg Leu Cys
1               5                   10                  15
```

<210> SEQ ID NO 24
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

```
Cys Gly Lys Pro Ile Trp Ser Cys Pro Met Thr Pro Asn Leu Cys
1               5                   10                  15
```

```
<210> SEQ ID NO 25
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Cys Gly Tyr Ser Leu Leu Thr Cys Thr Trp Lys Glu Trp Asp Cys
1               5                   10                  15

<210> SEQ ID NO 26
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Cys Arg Ala Ser Ala Gly Gln Cys Asn Pro Asp Pro Lys Leu Cys
1               5                   10                  15
```